(12) United States Patent
Schmaus et al.

(10) Patent No.: US 8,203,016 B2
(45) Date of Patent: *Jun. 19, 2012

(54) ANTHRANILIC ACID AMIDES AND DERIVATIVES THEREOF AS COSMETIC AND PHARMACEUTICAL AGENTS

(75) Inventors: Gerhard Schmaus, Höxter-Bosseborn (DE); Holger Joppe, Dassel (DE); Martinia Herrmann, Holzminden (DE); Christopher Sabater-Lüntzel, Holzminden (DE); Tobias Vössing, Beverungen (DE)

(73) Assignee: Symrise AG, Holzminden (DE)

( * ) Notice: Subject to any disclaimer, the term of this patent is extended or adjusted under 35 U.S.C. 154(b) by 804 days.

This patent is subject to a terminal disclaimer.

(21) Appl. No.: 10/535,985

(22) PCT Filed: Nov. 20, 2003

(86) PCT No.: PCT/EP03/12990
§ 371 (c)(1),
(2), (4) Date: May 24, 2005

(87) PCT Pub. No.: WO2004/047833
PCT Pub. Date: Jun. 10, 2004

(65) Prior Publication Data
US 2006/0089413 A1   Apr. 27, 2006

(30) Foreign Application Priority Data
Nov. 25, 2002 (DE) .................. 102 54 872

(51) Int. Cl.
C07C 207/00 (2006.01)
C07C 205/00 (2006.01)
C07C 229/00 (2006.01)

(52) U.S. Cl. .............. 560/21; 560/45; 560/46; 562/435; 562/452; 562/453; 562/455

(58) Field of Classification Search ............. 560/21, 560/45, 46; 562/435, 452, 453, 455
See application file for complete search history.

(56) References Cited

U.S. PATENT DOCUMENTS

| | | | |
|---|---|---|---|
| 3,940,422 A | 2/1976 | Harita | |
| 4,070,484 A * | 1/1978 | Harita et al. | 514/563 |
| 4,337,270 A * | 6/1982 | Noda et al. | 514/535 |
| 4,347,188 A * | 8/1982 | Kirino et al. | 549/436 |
| 4,486,597 A | 12/1984 | Iizuka | |
| 4,587,356 A | 5/1986 | Iizuka | |
| 2008/0008660 A1* | 1/2008 | Rabenhorst et al. | 424/45 |

FOREIGN PATENT DOCUMENTS

| | | |
|---|---|---|
| EP | 0391002 | 11/1989 |
| EP | 0399814 * | 11/1990 |
| JP | 49-093335 | 9/1974 |
| JP | 51026839 * | 3/1976 |
| JP | 57038759 | 3/1982 |
| JP | 57-036905 | 6/1982 |
| JP | 58-038444 | 3/1983 |
| JP | 60146856 | 8/1985 |
| JP | 63-088160 | 4/1988 |
| JP | 02-264716 | 10/1990 |
| JP | 08143525 * | 6/1996 |
| JP | 9-104607 | 4/1997 |
| JP | 2000-507269 | 6/2000 |
| JP | 2001-097865 | 4/2001 |
| JP | 2001-122730 | 5/2001 |
| WO | WO 97/35480 | 10/1997 |
| WO | 0067626 | 11/2000 |
| WO | WO 00/67626 | 11/2000 |

OTHER PUBLICATIONS

Blaamer et al, Structure-activity relationship of isolated avenanthramide alkaloids, J of Natural Products, 1994, 57(8), p. 1145-51.*
Hauteville et al, Novbel synthesis of dianthalexine(phytoalexin)analogs, J. of Heterocyclic Chemistry, 1988, 25(3), p. 715-718.*
Steiger Robert, Benzoylation of Amino Acids,1944, J. of Organic Chemistry, vol. 9, p. 396-400.*
Ponchet et al, Dianthramides (N-benzoyl and N-paracoumarylanthranilic acid derivatives) from elicted tissues of *Dianthus caryophyllus*, 1988, Phytochemisty, 27(3), 725-30 (abstract page).*
Leader et al, Uncoupling of oxdative phosphorylation by some salicylamide derivatives, 1966, Biochemical Pharmacology, 15(9), 1379-87 (abstract page).*
Naruto et al, synthesis of yokonoside and its related compounds, 1976, 96(8), p. 945-51, (abstract p. 1).*
Kirino et al, Structure-activity Relationships of Fungicidal N-benzoylanthranilic Esters, Agricutural Biol. Chem., 1980, 44(9),p. 2149-2153.*
Ponchet et al, Dianthramides (N-benzoyl and N-paracoumarylanthranilic acid derivatives)from elicited tissues of *Dianthus caryophyllus*, Phytochemistry, 1988, 27(3), 725-30, abstract page.*

(Continued)

*Primary Examiner* — Taylor Victor Oh
(74) *Attorney, Agent, or Firm* — Roylance, Abrams, Berdo & Goodman, L.L.P.

(57) ABSTRACT

The use of specific compounds of the Formula 1 (and also corresponding mixtures)

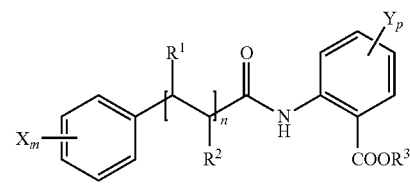

in particular as cosmetic agents for the inhibition of the substance P-induced release of histamine from mast cells is described.

4 Claims, No Drawings

OTHER PUBLICATIONS

Morlyan et al, N-(3,4,5-Trimethoxybenzoyl)-p-aminobenzoic acid, 1969, Metody Poluch . Khim. Reaktiv. Prep. No. 20, p. 121-123, abstract page .*
Ponchet et al, Dianthramides (N-benzoyland N-paracoumarylanthranilic acid derivatives) from elicited tissues of *Dianthus caryophyllus*, Phytochemistry, 1988, 27(3), p. 725-30.*
Crombie, Leslie; Mistry, Jaysheree, The phytoalexins of oat leaves: 4h-3,1-benzoxazin-4-ones or amides?, Tetrahedron Letters, 1990, Vo. 31, No. 18, p. 2647-8.
Van der Stelt, C. et al., The Hofmann Degradation of 4-Hydroxyphthalimide, Recueil des Travaux Chimiques des Pays-Bas et de la Belgique, 1953, vol. 72, p. 195-201.
Ma, JunJiang et al., Effect of N-(3', 4', 5'-Trimethoxycinnamoyl)ortho-Aminobenzoic Acid on Antigen-induced Contraction of Guinea-pig Ileum and the Degranulation of and Histamine Release from Mast Cells, Journal of Chinese Pharmaceutical Sciences, 1992, vol. 1, No. 1, p. 41-45.

Ishihara A et al., "induction of hydroxyanthranilate hydroxycinnamoyl transferase activity by oligo-N-acetylchitooligosaccharides in oats", Phytochemistry, Pergamon Press, GB, BD. 47, Nr. 6, 1998, Seiten 969-974.
Database Chemabs [Online] Chemical Abstracts Service, Columbus, OH, Ma, Junjiang et al. Effects of N-(3',4',5'-trimethoxycinnamoyl) ortho-aminobenzoic acid on antigen-induced contraction of guinea pig ileum and the degranulation of an histamine release from mast cells, 1992.
Database Chemabs [Online] Chemical Abstracts Service, Solumbus, OH, Yin K. et al., Interaction between terbutaline and ethyl-2-(4-'carboxybenzamido)-4-propionamidobenzoate sodium salt in tracheal smooth muscle relaxation of guinea pig, 1990.
Ghelardoni, Mario et al., Quaternary salts of substituted 2-aminoethylN-benzoylaminobenzoate. New class of smooth muscle relaxant agents, Journal of Medicinal Chemistry, 16(9), 1063-5 CODEN: JMCMAR; ISSN: 0022-2623, 1973.

* cited by examiner

ANTHRANILIC ACID AMIDES AND DERIVATIVES THEREOF AS COSMETIC AND PHARMACEUTICAL AGENTS

The present invention relates to specific uses of compounds of the Formula 1 or of mixtures of two or more different compounds of the Formula 1.

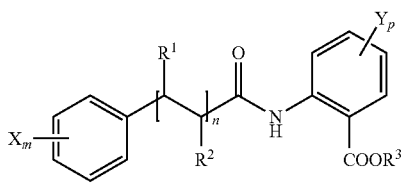

The invention also relates to selected compounds of the Formula 1 that were not known hitherto.

A first aspect of the present invention relates to a use of a compound of the Formula 1 or of a mixture of two or more different compounds of the Formula 1 as a cosmetic agent for inhibiting the release of histamine from mast cells that is induced by the substance P or for the preparation of a medicament for the inhibition of the release of histamine from mast cells that is induced by the substance P.

In this context the following applies for the compound of the Formula 1 and for each compound of the Formula 1 in the mixture:

m=0, 1, 2 or 3,
p=0, 1 or 2,
n=0, 1 or 2, with the proviso that, when n=1 or 2, the sum of p+m >0,
where, when n=1 or 2, $R^1$ and $R^2$, in each case in pairs, in each case denote H or together denote a further chemical bond (such as, for example, in cinnamic acid derivatives);
where, when m=1, 2 or 3, each X, independently of the others, denotes OH, Oalkyl or Oacyl,
where, when p=1 or 2, each Y, independently of the others, denotes OH, Oalkyl or Oacyl,
with the proviso that, when p+m >0, X or Y has been selected at least once from the group that consists of OH and Oacyl;
$R^3$=H or alkyl (in particular —$CH_3$, as well as straight-chain or branched alkyl chains with 2 to 30 C atoms)

In this context $R^3$=H for the corresponding pharmaceutically acceptable composition.

In this context, a compound of the Formula 1 can be in the form of an arbitrary isomer or mixture of isomers, thus for example, for n=1 and $R^1$, $R^2$=further chemical bond, in the form of the cis or trans-isomer.

For X or Y=Oacyl, preferably: acyl=CO—R where R=—$CH_3$, or a straight-chain or branched alkyl radical with 2-30 C atoms.

Mast cells play an essential role in allergic and inflammatory processes since, after corresponding stimulation, they release mediators such as histamine that to a large extent are responsible for symptoms such as itching (pruritus), pain or reddening reactions. Numerous studies have been able to show that the neuropeptide substance P, which is released by nerve ends in the skin, gives rise to a degranulation of mast cells. Thus, substance P can be regarded as one of the most important connecting links between the peripheral nerve system and symptoms such as inflammatory processes, itching and pain.

In the pharmaceutical and cosmetics industry there is an ongoing need for histamine release inhibitors. The uncontrolled release of high histamine concentrations is accompanied by symptoms such as itching, pain or reddening reactions. A clear correlation between histamine release and severe itching has been established in particular in the case of urticaria (nettle rash). The name urticaria is historically derived from the symptoms, which can be observed after contact of the skin with stinging nettles (latin name: *Urtica dioica* L.) (itching, burning and the development of weals). In this particular case, inter alia, histamine already contained in the stinging nettle, which is stored in special secretion organs and after contact with the skin is injected into the skin via the so-called stinging hairs, which are in the form of an injection needle, has an effect. The result is reddening, itching and the development of weals.

One feature is common to the various forms of urticaria, i.e. the activation of a special type of cell, the so-called mast cells. Mast cells can also be said to be the "fire brigade" or "border police" of the human body. They are to be found particularly frequently in locations where we come into direct contact with our environment, that is to say, as well as in the skin, also in the mucus membranes of the gastrointestinal tract and the respiratory tract. Activation of the mast cells by various mediators (immunoglobulins such as IgE or neuropeptides such as substance P) can be accompanied by severe inflammatory reactions, itching and severely allergic reactions extending to anaphylactic shock. For this purpose the mast cells produce a wide variety of products, including histamine. These products are stored by the cells in storage vessels, the so-called granula, and on activation are released in a large quantity into the skin. This, in turn,—and histamine has a particularly important role here—leads to the blood vessels becoming "leaky" at the point in the skin concerned and blood constituents (mainly fluid) penetrating into the tissue. A weal is produced as a result. In addition, widening of the blood vessels (vasodilation) takes place. Consequently, there is greater perfusion of blood through the skin regions concerned, which leads to reddening. The production of itching is explained as follows: on the one hand, the liberation of histamine from mast cells leads directly to itching. On the other hand, histamine and other mast cell products stimulate nerve fibres in the skin. This stimulation now has the result that the nerve fibres release substances that initiate itching (so-called neuropeptides). These neuropeptides (for example substance P) are, in turn, good mast cell activators, so that the stimulation of nerves by mast cells results in a stimulation of mast cells by nerves. In the skin and in mucous membranes, mast cells are preferably localised in the immediate vicinity of vessels and nerves. Thus, it is no surprise that the communication between the "neighbours" mast cells, vessel cells and nerve fibres functions extremely well.

Itching, which is partly to be ascribed to the release of high concentrations of histamine from mast cells, can arise in various illnesses. These include essentially allergic skin reactions (food allergies, chemicals), pruritus (nettle rash), contact with plants (for example stinging nettles), insect bites, psoriasis, infections and minor burns, healing injuries, physical stimuli, such as heat or mechanical friction and nickel allergy.

Surprisingly, it has been found in extensive research carried out by the Applicant that the abovementioned compounds of the Formula 1 and mixtures of two or more different compounds of the Formula 1 are outstandingly suitable for inhibiting the release of histamine from mast cells induced by substance P. Selected research results are summarised further below in the form of examples and tables.

Amongst the compounds of the Formula 1 that can be used according to the invention, certain sub-groups and individual substances are particularly suitable for inhibiting the release of histamine from mast cells induced by the substance P. These preferred sub-groups and individual substances can be seen from the dependent claims, the examples below and the associated tables.

According to a second aspect of the present invention, it has been found, surprisingly, that certain compounds of the Formula 1 or mixtures of two or more different compounds of the Formula 1 can be used not only for the inhibition of the release of histamine from mast cells induced by the substance P but also, more generally, for the treatment or prevention of itching (pruritus), skin reddening, development of weals and/ or allergic skin reactions (and also for the preparation of corresponding medicaments).

In general it is true that the compounds of the Formula 1 indicated above as suitable for inhibition, according to the invention, of the release of histamine from mast cells induced by the substance P, can also be used for the more general purpose of the treatment or prevention of itching, skin reddening, development of weals or allergic skin reactions.

However, to this extent as well, certain compounds of the Formula 1 are preferred, which can be seen from the dependent claims, the examples and the associated tables.

In this context it is pointed out that itching is not only related to the mechanisms indicated above, but is also brought into relation with dry skin, senile skin, mechanically or chemically stressed skin or skin stressed by sunlight. Furthermore, psychological factors such as anxiety or stress can cause itching. Soaps, cleaning agents and solvents that place a severe stress on the skin can lead to a disturbed hydrolipid film and cause itching reactions as a result. Itching can also arise during the healing process of injuries or burns (for example after shaving or after sunburn), so that here as well the application of cosmetic formulations that prevent or alleviate itching can contribute to preservation of an optimum physiological condition of the skin. In addition, there is the broad field of cosmetic products that are used on aging skin. Although the fundamental biochemical processes of itching and reddening reactions have not been clarified in detail, there are findings that histamine plays an essential role here as well.

It is therefore easy to comprehend that there is considerable interest in pharmacy and in the cosmetics industry in discovering active compounds that inhibit the release of histamine from mast cells and/or can be used for the treatment or prevention of itching, skin reddening, development of weals or allergic skin reactions.

The compounds of the Formula 1 according to the invention or the mixtures of two or more different compounds of the Formula 1 can be in the form of a constituent of a plant extract, which has been subjected to concentration (after-treatment) if necessary. In particular, the plant extract, which has been subjected to concentration, can be an extract from plants from the genus Avena, Dianthus, Silene or Melandrium, in particular oat extracts or carnation extracts.

If a plant extract is concentrated, this preferably ensures that the proportion of one or more compounds of the Formula 1 relative to the proportion of other extracted components is increased, compared with the extract that has not been concentrated.

If a plant extract is after-treated, this preferably ensures that the proportion of one or more compounds of the Formula 1 relative to the proportion of other extracted components is increased, compared with the extract that has not been after-treated.

Although this is not necessary in all cases, it is nevertheless in some cases advantageous to use an isolated and purified compound of the Formula 1 or an isolated and purified mixture of two or more different compounds of the Formula 1 for the said intended uses. The isolation and purification of compounds of the Formula 1 or corresponding mixtures from a plant extract are to be regarded as an after-treatment in which the proportion of compounds of the Formula 1 relative to the proportion of other extracted compounds is increased.

Finally, according to a further aspect, the present invention also relates to selected compounds of the Formula 1 that can be used for the intended purposes and were not known hitherto. These novel compounds according to the invention can be seen from the appended tables.

With regard to the state of the art, the following is pointed out:

Inter alia, the following therapeutic measures are already known for the alleviation of weakly pronounced itching: medicinal oil baths containing soya bean oil (Balneum hermal), liquid paraffin (oleatum fat) or γ-linolenic acid (linola fat oil bath), body creams (W/O emulsions in the form of lotions), such as, for example, Bepanthenol Roche Lotion F or Eucerin cum aqua, body oils containing almond or jojoba oil and preparations containing moisture retention factors, such as, for example, urea or salicylic acid. In the case of strongly pronounced exanthemata/weals, steroid-containing external agents are applied, for example.

Active compounds which have an itch-alleviating activity based on a targeted inhibition of the mediator-induced liberation of histamine from mast cells include, for example, disodium chromogycate, verapamil, ketotifen or tranilast. The substance known under the common name Tranilast is N-(3, 4-dimethoxy-cinnamoyl)anthranilic acid, a natural anthranilic acid amide occurring in the Chinese medicinal plant Nandina domestica, which, however, does not fall under Formula 1.

Possibilities for the use of tranilast in the case of allergic reactions, such as bronchial asthma, allergic rhinitis, allergic conjunctivitis, food allergies, urticara or atopic dermatitis are reported in various patents and publications (DE 2402398; EP 0074725; U.S. Pat. No. 4,070,484; H. Shioda et al., Allergy 34, 213-119 (1979); M. Kojima et al., Oyo Yakuri 28(4), 623-628 (1984), Azuma et al., Br. J. Pharmacol. Vol. 58, p. 483-488, (1976); Koda et al., Int. Archs. Allergy appl. Immun. Vol. 77, p. 244-245, (1985); Komatsu et al., Japan J. of Pharmacol. Vol. 46, 43-51,(1988); Hachisuka et al, Arch. Dermatol. Res. Vol. 280, p. 158-162, (1988).

As Komatsu et al report, tranilast inhibits the antigen-(DNP ascaris; monoclonal IgE antibody with 2,4-dinitrophenyl-specificity) induced release of histamine from mast cells in the concentration range of $10^{-3}$ to $10^{-5}$M. It was possible to achieve 50% inhibition of the histamine release at a concentration of approximately $10^{-4}$ M. On the other hand, the influence of other anthranilic acid amides on the inhibition of the release of histamine from mast cells was not described in the publication.

Hachisuka et al. (Arch. Dermatol. Res. Vol. 280, p. 158-162; 1988) investigated the influence of various active compounds on the inhibition of the substance P-induced release of histamine from mast cells. Here the activity of disodium chromogylcate (sic), ketotifen and tranilast was compared. It was possible to achieve 50% inhibition of the substance P-induced histamine release only at a relatively high concentration of approximately $10^{-3}$ M. For a molecular weight of tranilast of 327, $10^{-3}$M corresponds to a concentration of 327 µg/ml or 327 ppm. The value for DSCG (disodium cromoglycate), a known antiallergic agent, was in a comparable concentration range (41% inhibition at $10^{-3}$ M). Other anthranilic acid amides were not investigated in more detail within the framework of this research work either.

Kojima Masami et al. (Oyo Jakuri, 28(4), p. 623-28; 1984) describe the anti-allergic action of other anthranilic acid amides, such as, for example, a tranilast demethylated in the 4-position (N-(3-methoxy,(sic)4-hydroxycinnamoyl)anthranilic acid), which, however, is said to have an inhibitory effect only equal to that of tranilast.

In U.S. Pat. No. 4,070,484 it is described that the oral application of monosubstituted N-(4-hydroxycinnamoyl)anthranilic acid in a dose of 200 mg/kg effects a 36.7% inhibition of antigen-induced destruction of rat mast cells, in contrast with which the corresponding (dimethylated) tranilast (N-(3,4-dimethoxycinnamoyl)anthranilic acid) displays a distinctly higher inhibition rate, i.e. 46.1%, under identical test conditions. Comparative values relating specifically to the inhibition of the substance P-induced release of histamine from mast cells are not given in the document.

Anthranilic acid amides are described as constituents of certain plants, such as, for example, oats (*Avena sativa*) or carnations (*Dianthus* sp.).

The avenanthramides of oats are acid amides consisting of unsubstituted or substituted anthranilic acid partial structures and unsubstituted or substituted cinnamic acid partial structures, whilst, on the other hand, the acid amides in carnation species are essentially composed of anthranilic acid partial structures and benzoic acid partial structures. Plant physiological studies showed that both the so-called avenanthramides of oats and also the so-called dianthramides in carnations act as phytoalexins and are formed by the plant after microbial infestation as part of a defence mechanism.

The use of oat extracts to alleviate itching has long been known in folk medicine and is mentioned in the following documents: Hagers Handbuch der Pharmazeutischen Praxis, Vol. 4, published by R. Hänsel, K. Keller, H. Rimpler, G. Schneider, Springer Verlag, Berlin, 1992, p. 437-446; US Federal Register Oct. 3, 1989; 54, 190 proposed rules, pp 40808-40811; Bundesanzeiger No. 193, 15.10.1987). The use of specific yeast extract fractions with an enriched content of anthranilic acid amides to alleviate itching and skin reddening has been described in a more recent publication (J. Vollhardt et al., Proceedings of the XXIst IFSCC International Congress, Berlin, Sep. 11-14, 2000, p. 395; Verlag für Chemische Industrie, H. Ziolkowsky GmbH Augsburg Germany). However, this publication does not report which anthranilic acid amide or which anthranilic acid amides from the group of the so-called oats avenanthramides, which contains more than 30 substances, is/are involved in the alleviation of reddening reactions and itching.

The present invention is based on extensive studies, in particular on the following aspects:

Structure/activity considerations for identification of anthranilic acid amides with a reddening- and itch-alleviating action.

Preparation of plant extracts with a high content of specific, highly effective anthranilic acid amides, in particular preparation of specific oat and carnation extract fractions, and also of purified isolated active compounds, in particular from oats and/or carnations.

Synthesis of anthranilic acid amides with an itch-alleviating action.

The aim of the said studies was to make available particularly active compounds in preferably highly pure form, so that they can be used in pharmaceutical or cosmetic products free from any toxicologically or dermatologically critical subsidiary constituents (synthesis by-products or plant extract subsidiary constituents).

In general, it was to be borne in mind here that the substances to be used in cosmetic and/or pharmaceutical products should be toxicologically acceptable,
well tolerated by the skin,
stable (in particular in the customary cosmetic and/or pharmaceutical formulations),
preferably odourless and
able to be produced inexpensively (i.e. using standard processes and/or starting from standard precursors)

in the concentration range relevant for activity.

Preferred embodiments of the uses according to the invention and also compounds according to the invention can be seen from the following examples and the associated tables:

1. Synthesis of Anthranilic Acid Amides of the Formula 1

EXAMPLE 1

Synthesis of cinnamoylanthranilic acid derivatives that are unsubstituted or substituted in the nucleus, taking N-(4-hydroxycinnamoyl)anthranilic acid (avenanthramide D, 10; cf. Table 1a) as an example

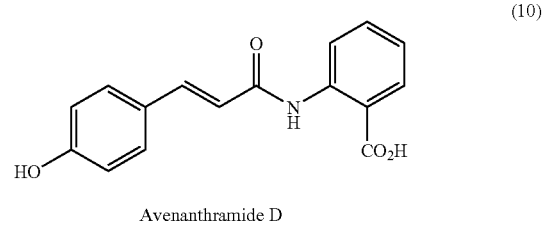

Avenanthramide D 15 g (91 mmol) 4-hydroxycinnamic acid, 50 ml acetic anhydride and 0.5 ml pyridine are stirred at room temperature for 20 h. The mixture is poured into ice-water and the precipitated 4-acetoxycinnamic acid is separated off and dried (18 g). 15 g (77 mmol) 4-acetoxycinnamic acid are initially introduced and 15 g (100 mmol) thionyl chloride added dropwise. The mixture is then stirred for 1 h under reflux, the excess thionyl chloride is separated off by distillation and 50 ml toluene is added to the acid chloride. A solution of 7 g (51 mmol) anthranilic acid in 70 ml pyridine is added and the reaction mixture is stirred for 2 h at 90° C. After cooling, the reaction mixture is poured into ice-water and extracted with ethyl acetate, the organic phase is washed with water until neutral and the solvent is removed under vacuum. 300 g 10% sodium hydroxide solution is added to the residue and the mixture is stirred under reflux for 1-2 h. After cooling, the mixture is acidified with concentrated hydrochloric acid and extracted with ethyl acetate and the organic phase is washed with water until neutral and the solvent is removed under vacuum. The crude product (23 g) is recrystallised by repeated dissolving, with heating, in ethanol, cooling and precipitation by addition of water and is further purified by RP-18 medium-pressure chromatography (column: YMC ODS-AQ, eluent: methanol/water 50:50+0.5 ml acetic acid/I, λ 280 nm) (yield: 1.1 g 10, purity: 95%).

Spectroscopic data: $^1$H-NMR (300 MHz, $D_6$ acetone): 8.91 (1 H, dd, J=1.2 and 8.5 Hz), 8.14 (1H, dd, J=1.7 and 8.1 Hz), 7.67 (1H, d, J=15.4 Hz), 7.61 (1 H, m), 7.60 (2 H, d, J=8.7 Hz), 7.16 (1 H, m), 6.92 (2 H, d, J=8.7 Hz), 6.64 (1 H, d, J=15.4 Hz).—$^{13}$C-NMR (75.5 MHz, $D_6$ acetone): 170.5 (s), 165.3 (s), 160.2 (s), 143.3 (s), 142.7 (d), 135.2 (d), 132.2 (d), 130.8 (2C, d), 127.3 (s), 123.0 (d), 120.9 (d), 119.8 (d), 116.6 (2C, d), 115.8 (s).

EXAMPLE 2

Catalytic hydrogenation of cinnamoylanthranilic acid derivatives that are unsubstituted or unsubstituted in the nucleus to give the corresponding dihydro compound (8, Table 1a) taking N-(4-hydroxycinnamoyl)-anthranilic acid (avenanthramide D, 10) as an example.

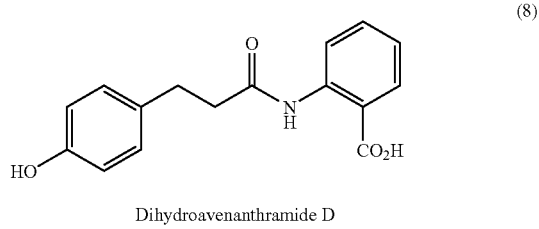

(8)

Dihydroavenanthramide D 140 mg N-(4-hydroxycinnamoyl)anthranilic acid (avenanthramide D, 10) are taken up in 20 ml ethanol and quantitatively hydrogenated with hydrogen in the presence of palladium (5% on active charcoal).

Spectroscopic data: $^1$H-NMR (300 MHz, $D_6$ acetone): 8.68 (1 H, dd, J=0.8 and 8.4 Hz), 8.08 (1 H, dd, J=1.5 and 7.8 Hz), 7.59 (1 H, m), 7.15 (1 H, m), 7.12 (2 H, d, J=8.5 Hz), 6.77 (2 H, d, J=8.5 Hz), 2.95 (2 H, t, J=7.6 Hz), 2.75 (2 H, t, J=7.6 Hz).

2. Extraction of Anthranilic Acid Amide Fractions from Plants

EXAMPLE 3

Extraction of an anthranilic acid amide-containing extract from cultivated oats (*Avena sativa*)

143 kg ethanol/water 7:3 (m/m) are added to 9 kg cultivated oats and the mixture is macerated for 3 days at room temperature. After filtration, the extract is concentrated to the aqueous phase under vacuum (17.4 kg, solids content: 2.5%, Σ avenanthramides A, B & C in dry extract: 0.093%).

The aqueous solution is extracted in portions (2 kg) by stirring with Amberlite XAD-16 (270 g). The adsorber resin is separated off via a frit, washed with water and eluted with methanol/water 1:1 (V/V). The combined eluates are freed from solvent under vacuum. Dry extract: 8.5 g, Σ avenanthramides A, B & C. 1.2%.

This dry extract is taken up in ethanol/water 1:1 (V:V) and adjusted to an avenanthramide content Σ A, B & C of 500 ppm by dilution with ethanol/water 1:1 (V:V).

3. Activity Studies on the Inhibition of Substance P-Induced Release of Histamine from Mast Cells by Anthranilic Acid Amides of the General Formula 1.

3.1. Synthetic Anthranilic Acid Amides
Test Products

Stock solutions: avenanthramides 2 to 19 (structural formulae: see Table 1a) and dianthramides 20-29 (structural formulae: see Table 1b); concentration: 1% in ethanol; storage before use at 4° C.)
Reagents
Substance P: BACHEM.
Test Design:
Mast cells from the peritoneal tissue of rats were isolated by centrifuging on metrizamide and stimulated with substance P (10 μM). Calcium chloride served as positive control.

Sample Preparation: Test and Reference Substances:
The synthetically prepared avenanthramides and dianthramides of the Formulae 2 to 29 (cf. Tables 1a/1b) were diluted with buffer medium to the final concentrations (0.5; 5 and 50 ppm, see Tables 1a/1b), corresponding to an ethanol concentration of 0.5; 0.05 and 0.005% (V/V), respectively. Calcium chloride, which served as positive control, was likewise diluted with buffer medium so that solutions in the concentration range from $10^{-8}$ to $10^{-2}$ M were available.
Incubation Protocol:
Test system: The final test solutions were incubated for 2 minutes in the presence of substance P and of the reference substance ($CaCl_2$) or of the particular sample to be tested (incubation temperature: 37° C.). Cells that had been incubated in the absence of substance P and reference or sample substance served as blank.
Determination of the Total Histamine Content After Cell Lysis:
The reaction solutions were first freed from cell constituents by centrifuging. The histamine present in the supernatant liquor was then converted to a derivative with OPT and the fluorescence of the solutions was determined photometrically (fluorometer Cytofluor 2350).
Result:
Calcium chloride inhibited substance P-induced release of histamine from mast cells depending on the concentration. It was possible to achieve 50% inhibition with a calcium chloride concentration of 639 μM. This corresponds to the value to be expected and thus validates the fundamental test design.

The values for the various avenanthramides and dianthramides are given in Table 1a/1b as % inhibition based on the histamine content of cells stimulated with substance P.

3.2. Anthranilic Acid Amide Fraction from Oat Seeds in Direct Comparison with a Reconstituted Product Consisting of Identical Mass Ratios of Synthetically Prepared Oat Anthranilic Acid Amides
Test Products Stock solutions: GS-101100-A and GS-101100-B (composition of the samples: see Table 2; concentration: 500 ppm E avenanthramides A, B and C in glycerol; storage before use at 4° C.)
Reagents
Substance P: BACHEM.
Test Design:
Mast cells from the peritoneal tissue of rats were isolated by centrifuging on metrizamide and stimulated with substance P (10 μM). Calcium chloride served as positive control.
Sample Preparation: Test and Reference Substances:
The GS-101100-A and GS-101100-B samples were diluted with buffer medium to the final concentrations (0.5; 5 and 50 ppm, see Table 2), corresponding to an ethanol concentration of 0.1; 1 and 10% (V/V) respectively. Calcium chloride, which served as positive control, was likewise diluted with buffer medium so that solutions in the concentration range from $10^{-5}$ and (sic) $10^{-2}$ M were available.
Incubation Protocol:
Test system: The final test solutions were incubated for 2 minutes in the presence of substance P and of the reference substance ($CaCl_2$) or of the particular sample to be tested (incubation temperature: 37° C.). Cells that had been incubated in the absence of substance P and reference or sample substance served as blank.
Determination of the Total Histamine Content after Cell Lysis:
The reaction solutions were first freed from cell constituents by centrifuging. The histamine present in the supernatant liquor was then converted to a derivative with OPT and the fluorescence of the solutions was determined photometrically (fluorometer Cytofluor 2350).
Result:

Calcium chloride inhibited substance P-induced release of histamine from mast cells depending on the concentration. Within this test series, it was possible to obtain a 50% inhibition at a calcium chloride concentration of 432 µM. This corresponds to the value to be expected and thus validates the fundamental test design.

The values for the various avenanthramides are given in Table 2 as % inhibition based on the histamine content of cells stimulated with substance P without the addition of inhibitors.

4. Results and Structure/Activity Considerations
4.1. Synthetic Anthranilic Acid Amides Results of tests on selected, highly pure anthranilic acid amides with cinnamic acid partial structure and dihydrocinnamic acid partial structure (avenanthramides) show that there are significant differences in the activity depending on the substitution sample. The highest activity, i.e. complete inhibition of the histamine release, is achieved with substances of the Formulae 2 and 3 (cf. Table 1a), which have vicinal hydroxyl groups in the 3- and 4-positions of the cinnamic acids/dihydrocinnamic acid part. On the other hand, further hydroxyl groups in the anthranilic acid part do not lead to an additional increase in activity here. This is shown by the virtually identical inhibition data for substance 2 (7%, 80% and 108% for an active substance concentration of 0.5, 5 and 50 ppm, respectively, cf. Table 1a) and substance 3 (11%, 62% and 106% for an active substance concentration of 0.5; 5 and 50 ppm, respectively, cf. Table 1a). Thus, an inhibition of the histamine release of >50% can already be achieved with a dosage of 5 ppm, whereas, on the other hand, tranilast (substance 15, Table 1a) is capable of only 21% inhibition of the histamine release under identical test conditions, even in the highest dosage of 50 ppm.

An activity significantly higher than that of tranilast is also observed in the case of anthranilic acid amides with only one free hydroxyl group in the cinnamic acid/dihydrocinnamic acid part, and specifically especially when this is arranged in the 4-position of the cinnamic acid/dihydrocinnamic acid part constituent (Table 1a: substances 4-10). The percentage rate of histamine release inhibition for a dosage of 50 ppm is in the range of 37-49% here. Here again, additional substituents in the anthranilic acid part do not lead to any significant increase in activity. Thus, within the group of anthranilic acid amides with only one free hydroxyl group in the cinnamic acid/dihydrocinnamic acid part as well, there is a distinctly higher activity in direct comparison with tranilast.

An activity higher than that of tranilast is also observed with anthranilic acid amides with only one free hydroxyl group in the anthranilic acid residue, and specifically especially when this is in the 4-position of the anthranilic acid residue (cf. Table 1: substances 11-13). The percentage rate of the histamine release inhibition at a dosage of 50 ppm is in the range of 30-36% here.

The substances 2-13 are illustrative representatives of a preferred sub-group of compounds of the Formula 1, for which:
n=1 and
furthermore:
m=1, 2 or 3,
with the proviso that X has been selected at least once from the group that consists of OH or (sic) Oacyl.
and/or
p=1 or 2,
with the proviso that Y has been selected at least once from the group that consists of OH and Oacyl.

Substances 14-19, which also include tranilast (substance 15), exert an inhibitory effect in respect of histamine release that is no longer satisfactory, compared with the substances designated above.

The comparatively low activity of tranilast agrees with the research carried out by Hachisuka et al. (Arch Dermatol Res Vol. 280, p. 158-162; 1988). The authors were able to establish a 50% inhibition of the histamine release only at a concentration of 327 ppm. Apparently, the alkylation of the vicinal hydroxyl groups in the cinnamic acid part or dihydrocinnamic acid part is accompanied by a significant reduction in activity.

Corresponding structure/activity considerations within the group of compounds with a benzoic acid partial structure (dianthramides) led to comparable results. Here the compounds with two vicinal hydroxyl groups in the 3- and 4-positions of the benzoic acid residue (cf. Table 1b; cf. in particular substance 20) have the greatest activity. Dianthramides with at least one free hydroxyl group in the benzoic acid part of the molecule also show an activity that, although it is slightly weaker, is nevertheless good.

Compounds 20-29 listed in Table 1b are illustrative representatives of a preferred sub-group of compounds of the Formula 1, for which n=0.

4.2 Anthranilic Acid Amide Fractions of Vegetable Origin

In addition to synthetically prepared avenanthramides and dianthramides, various plant extracts were also studied with regard to the suitability thereof for the inhibition of substance P-induced release of histamine from mast cells. Table 2 shows, by way of example, the results of the direct comparison of an oat extract (cf. Table 2: sample GS10100-A, oat extract standardised to 500 ppm Σ avenanthramides 3, 4 and 5; formulae: cf. also Table 1a;) and a synthetic reconstituted product containing a total of 500 ppm Σ synthetic avenanthramides 3, 4 and 5 (sample GS10100-B, cf. also Table 1a) in precisely comparable mass ratios.

The direct comparison of the two samples proves that the inhibition of the substance P-induced release of histamine from mast cells is essentially caused by the avenanthramides 3, 4 and 5 contained in oat extract (cf. Table 1a).

This finding shows, in general, that, in addition to synthetic compounds according to the invention, plant extracts and fractions prepared therefrom that contain these substances in a standardised amount can also preferentially be used as inhibitors of the substance P-induced release of histamine from mast cells and thus are able to prevent inflammation, reddening and itching reactions and/or to contribute to alleviating these.

5. Review of Selected Substances Already Known and Not Known Hitherto for Use as Histamine Release Inhibitors:

In Tables 3 and 4, on the one hand, substances not known hitherto and, on the other hand, substances already known that are preferably used as histamine release inhibitors are listed by way of example. Substances 2-29 are already in Tables 1a and 1b; substances 30-80 are not in these tables.

The substances contained in Tables 3 and 4 are all acids; however, it is pointed out that the corresponding esters (where $R^3$=alkyl instead of $R^3$=H) and the corresponding pharmaceutically acceptable salts can also be used in the same way.

6. Summary of the Test Results and Supplementary Remarks:

The tests carried out show, surprisingly, that the compounds of the Formula 1 according to the invention inhibit the substance P-induced release of histamine from mast cells in a use concentration that is considerably lower compared with tranilast and thus, because of the lower therapeutic use concentration and the lower toxicological risk potential associated therewith, can preferably be used as active compounds. The compounds and mixtures that can be used according to the invention can be highly pure synthesis products, pure isolated products from plant extracts, such as, for example, from oats (*Avena sativa*) or carnation species (*Dianthus* spec.) or specific extract fractions from plants such as oats (Avena sativa) or carnations (*Dianthus* sp.), which contain the compounds according to the invention, which are preferably to be used, in high concentration.

Instead of the compounds tested, compounds (precursors) in which the hydroxyl groups in the cinnamic acid/dihydrocinnamic acid part or in the benzoic acid part have been acylated, can preferably also be used (X or Y=Oacyl where acyl=CO—R where R=—$CH_3$, or a straight-chain or branched alkyl radical with 2-30 C atoms). In addition, precursors in which the carboxyl groups in the anthranilic acid part have been alkylated (where $R^3$=—$CH_3$, or straight-chain or branched alkyl radicals with chain lengths C 2 to 30) can preferably also be used. On topical application, corresponding acylated or alkylated compounds of the Formula 1 penetrate very well into deeper layers of the skin. Here they are cleaved by the non-specific esterases endogenously present in human and animal skin, so that the actual active principle is released only at the site of action.

Depending on the substance, the use concentration of the compounds of the Formula 1 that can be used according to the invention is in the concentration range of 0.0001 to 10% (m/m) and preferably in the concentration range of 0.001-1% (m/m), based on the total mass of a cosmetic or pharmaceutical end product ready for use.

The histamine release inhibitors, and in particular those of the avenanthramide and dianthramide type, used according to the invention can be incorporated without difficulty in conventional cosmetic or dermatological/keratological formulations such as, inter alia, pump sprays, aerosol sprays, creams, shampoos, ointments, tinctures, lotions, nail care products (for example nail varnishes, nail varnish removers, nail balsams) and the like. In this context it is also possible, and in some cases advantageous, to combine the histamine release inhibitors according to the invention with further active compounds, for example with other, optionally even synergistically intensifying, histamine release inhibitors or with anti-inflammatory substances and/or substances that reduce itching and reddening, the action of which is based on a different principle of action, such as, for example, the inhibition of the release of inflammation mediators (inter alia leucotrienes, prostaglandins or cytokins (sic)). In this context the cosmetic and/or dermato-logical/keratological formulations containing the histamine release inhibitors according to the invention can otherwise be of customary composition and serve for treatment of the skin and/or the hair in the sense of a dermatological or keratological treatment or of a treatment in the sense of care cosmetics. However, they can also be used in make-up products in decorative cosmetics.

Cosmetic formulations that contain the histamine release inhibitors according to the invention can also contain further anti-inflammatory active compounds or active compounds having a reddening- and itch-alleviating action. In this context all anti-inflammatory active compounds and active compounds that alleviate reddening and itching that are suitable or customary for cosmetic and/or dermatological applications can be used. Advantageously, the anti-inflammatory active compounds and active compounds alleviating reddening and/or itching that are used are steroidal anti-inflammatory substances of the corticosteroid type, such as, for example, hydrocortisone, dexamethasone, dexamethasone phosphate, methylprednisolone or cortisone, it being possible to expand the list by adding further steroidal anti-inflammatory agents. Non-steroidal anti-inflammatory agents can also be used. Oxicams, such as piroxicam or tenoxicam; salicylates, such as aspirin, Disalcid, Solprin or fendosal; acetic acid derivatives, such as diclofenac, fenclofenac, indomethacin, sulindac, tolmetin, or clindanac; fenamates, such as mefenamic, meclofenamic, flufenamic or niflumic; propionic acid derivatives, such as ibuprofen, naproxen, benoxaprofen or pyrazoles, such as phenylbutazone, oxyphenylbutazone, febrazone or azapropa-zone, may be mentioned here by way of example. Alternatively, natural anti-inflammatory substances and substances that alleviate reddening and/or itching can be used. Plant extracts, special highly active plant extract fractions and also highly pure active substances isolated from plant extracts can be used. Extracts, fractions and active substances from camomile, aloe vera, Commiphora species, Rubia species, willows, willow-herb and pure substances such as, inter alia, bisabolol, apigenin-7-glucoside, boswellic acid, phytosterols, glycyrrhizine, glabridin or licochalkon A are particularly preferred. The formulations containing histamine release inhibitors can also contain mixtures of 2 or more anti-inflammatory active compounds.

Cosmetic formulations that contain histamine release inhibitors according to the invention can also contain active compounds for preservation, it being possible to use all preservatives that are suitable or customary for cosmetic and/or dermatological applications. Advantageously, preservatives such as, inter alia, benzoic acid, the esters and salts thereof, propionic acid and salts thereof, salicylic acid and salts thereof, 2,4-hexanoic acid (sorbic acid) and salts thereof, formaldehyde and paraformaldehyde, 2-hydroxybiphenyl ether and salts thereof, 2-zincsulphidopyridine-N-oxide, inorganic sulphites and bisulphites, sodium iodate, chlorobutanolum, 4-hydroxybenzoic acid, the salts and esters thereof, dehydratcetic (sic) acid, formic acid, 1,6-bis(4-amidino-2-bromophenoxy)-n-hexane and salts thereof, the sodium salt of ethylmercury-(II)-thiosalicylic acid, phenylmercury and salts thereof, 10-undecylenic acid and salts thereof, 5-amino-1,3-bis(2-ethylhexyl)-5-methylhexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)urea, 4-chloro-m-cresol, 2,4,4'-trichloro-2'-hydroxy-diphenyl ether, 4-chloro-3,5-dimethylphenol, 1,1'-methylene-bis(3-(1-hydroxymethyl-2,4-dioximidazolidin-5-yl)urea), poly-(hexamethylene diguanide) hydrochloride, 2-phenoxyethanol, hexamethylentetramine, 1-(3-chloroallyl)-3,5,7-triaza-1-azonia-adamantane chloride, 1 (4-chloro-phenoxy)-1(1H-imidazol-1-yl)-3, 3-dimethyl-2-butanone, 1,3-bis-(hydroxy-methyl)-5,5-dimethyl-2,4-imidazolidinedione, benzyl alcohol, Octopirox, 1,2-dibromo-2,4-dicyanobutane, 2,2'-methylene-bis(6-bromo-4-chloro-phenol), bromochlorophene, mixture of 5-chloro-2-methyl-3(2H)-isothiazolinone and 2-methyl-3 (2H)isothiazlinone (sic) with magnesium chloride and magnesium nitrate, 2-benzyl-4-chlorophenol, 2-chloracetamide, chlorhexidine, chlorhexidine acetate, chlorhexidine gluconate, chlorhexidine hydrochloride, 1-phenoxy-propan-2-ol, N-alkyl($C_{12}$-$C_{22}$)trimethylammonium bromide and chloride, 4,4-dimethyl-1,3-oxazolidine, N-hydroxymethyl-N-(1,3-di (hydroxymethyl)-2,5-dioxo-imidazolidin-4-yl)-N'-hydroxymethylurea, 1,6-bis(4-amidino-phenoxy)-n-hexane and salts thereof, glutaraldehyde 5-ethyl-1-aza-3,7-dioxa-bi-cyclo(3.3.0)octane, 3-(4-chlorphenoxy)-1,2-propanediol, hyamine, alkyl-($C_8$-$C_{18}$)-dimethylbenzylammonium chloride, alkyl-($C_8$-$C_{18}$)-dimethylbenzylammonium bromide, alkyl-($C_8$-$C_{18}$)-dimethyl-benzyl-ammonium saccharinate, benzylhemiformal, 3-iodo-2-propinylbutyl carbamate, sodium hydroxymethylaminoacetate or sodium hydroxy-methylaminoacetate (sic) are chosen.

Further antibacterial or antimycotic active substances can also be used particularly advantageously in the cosmetic formulations that contain histamine release inhibitors according to the invention, it being possible to use all antibacterial or antimycotic active substances that are suitable or customary for cosmetic and/or dermatological applications. In addition to the large group of conventional antibiotics, in particular the products relevant for cosmetics, such as triclosan, climbazol, octoxyglycerol, Octopirox (1-hydroxy-4-methyl-6-(2,4,4-trimethylpentyl)-2(1H)-pyridone, 2-aminoethanol), chitosan, farnesol, glycerol monolaurate or combinations of the said substances, which, inter alia, are used against underarm odour, foot odour or dandruff, are advantageous here.

In addition, the synergistic mixtures of histamine release inhibitors according to the invention can also be used particularly advantageously in combination with perspiration-inhibiting active compounds (antiperspirants) for controlling body odour. Perspiration-inhibiting active compounds used are, in particular, aluminium salts, such as aluminium chloride, aluminium chlorohydrate, nitrate, sulphate, acetate etc. In addition, however, the use of zinc, magnesium and zirconium compounds can also be advantageous. Essentially the aluminium salts and—to a somewhat lesser extent—aluminium/zirconium salt combinations have proved their worth for use in cosmetic and dermatological antiperspirants. The partially neutralised aluminium hydroxychlorides, which are thus better tolerated by the skin but are not quite as effective, are also worthy of mention. In addition to aluminium salts, further substances can also be used, such as, for example, a) protein-precipitating substances such as, inter alia, formaldehyde, glutaraldehyde, natural and synthetic tanning agents and also trichloroacetic acid, which give rise to surface closure of the sweat glands, b) local anaesthetics (inter alia dilute solutions of, for example, lidocaine, prilocaine or mixtures of such substances) that switch off the sympathetic supply of the sweat glands by blocking the peripheral nerve paths, c) zeolites of the X, A or Y type, which in addition to reducing sweat secretion also act as adsorbents for bad odours, and d) botulinus toxin (toxin of the bacterium Chlostridium botulinum), which is also used in the case of hyperhidrosis, a pathologically increased sweat secretion, and the action of which is based on an irreversible blockage of the release of the transmitter substance acetylcholine relevant for sweat secretion.

A combination with (metal) chelating agents can also be advantageous in the cosmetic formulations that contain histamine release inhibitors according to the invention, it being possible to use all metal chelating agents that are suitable or customary for cosmetic and/or dermatological applications. (Metal) chelating agents that are preferably to be used are, inter alia, α-hydroxy fatty acids, phytic acid, lactoferrin, α-hydroxy acids, such as, inter alia, citric acid, lactic acid and malic acid, as well as humic acids, bile acids, bile extracts, bilirubin, biliverdin or EDTA, EGTA and derivatives thereof.

For use, the formulations containing histamine release inhibitors according to the invention are applied to the skin and/or the hair in an adequate amount in the manner customary for cosmetics and dermatological products. In this context cosmetic and dermatological formulations that contain a mixture according to the invention and additionally act as a sunscreen offer particular advantages. Advantageously, these formulations contain at least one UVA filter and/or at least one UVB filter and/or at least one inorganic pigment. In this context the formulations can be in various forms, such as are, for example, customarily employed for this type of formulation. Thus, they can be, for example, a solution, an emulsion of the water-in-oil (W/O) type or of the oil-in-water (O/W) type or a multiple emulsion, for example of the water-in-oil-in-water (W/O/W) type, a gel, a hydrodispersion, a solid stick or also an aerosol.

As mentioned, formulations that contain histamine release inhibitors according to the invention can advantageously be combined with substances that absorb UV radiation in the UVB range, the total amount of the filter substances being, for example, 0.01% (mlm) to 40% (m/m), preferably 0.1% to 10% (mlm), in particular 1.0 to 5.0% (m/m), based on the total weight of the formulations, in order to make available cosmetic formulations that protect the hair and/or the skin against the entire range of ultraviolet radiation. They can also serve as sunscreens for hair. If the formulations according to the invention contain UVB filter substances, these can be oil-soluble or water-soluble. Advantageous oil-soluble UVB filters are, for example: 3-benzylidenecamphor derivatives, preferably 3-(4-methylbenzylidene)camphor, 3-benzylidenecamphor; 4-aminobenzoic acid derivatives, preferably 2-ethylhexyl 4-(dimethyl-amino)benzoate, amyl 4-(dimethylamino)benzoate, esters of cinnamic acid, preferably 2-ethylhexyl 4-methoxycinnamate, isopentyl 4-methoxy-cinnamate; esters of salicylic acid, preferably 2-ethylhexyl salicylate, 4-isopropylbenzyl salicylate, homomenthyl salicylate, derivatives of benzophenone, preferably 2-hydroxy-4-methoxybenzophenone, 2-hydroxy-4-methoxy-4'-methyl-benzophenone, 2,2'-dihydroxy-4-methoxy-benzophenone, esters of benzalmalonic acid, preferably di(2-ethylhexyl)4-methoxybenzalmalonate, 2,4,6-trianilino-(p-carbo-2'-ethyl-1'-hexyloxy)-1,3,5-triazine. Advantageous water-soluble UVB filters are, for example, salts of 2-phenylbenzimidazole-5-sulphonic acid, such as the sodium, potassium or triethanolammonium salt thereof, and also the sulphonic acid itself; sulphonic acid derivatives of benzophenones, preferably 2-hydroxy-4-methoxybenzophenone-5-sulphonic acid and salts thereof; sulphonic acid derivatives of 3-benzylidenecamphor, such as, for example, 4-(2-oxo-3-bomylidenemethyl)benzenesulphonic acid, 2-methyl-5-(2-oxo-3-bomylidene-methyl)sulphonic acid and salts thereof and also 1,4-di(2-oxo-10-sulpho-3-bomylidenemethyl)-benzene and salts thereof (the corresponding 10-sulphato compounds, for example the corresponding sodium, potassium or triethanolammonium salt) and also benzene-1,4-di(2-oxo-3-bomylidenemethyl-10-sulphonic acid (sic).

The above list of the said UVB filters that can be used in combination with the histamine release inhibitors according to the invention should, of course, not be understood as definitive. It can also be advantageous to employ UVA filters, such as are customarily contained in cosmetic formulations. These substances are preferably derivatives of dibenzoylmethane, in particular 1-(4'-tert.-butylphenyl)-3-(4'-methoxy-phenyl) propane-1,3-dione and 1-phenyl-3-(4'-isopropylphenyl)propane-1,3-dione. The amounts used for the UVB combination can be used.

In cosmetic formulations, the histamine release inhibitors according to the invention can advantageously also be combined with further cosmetic auxiliaries, such as are customarily used in such formulations, thus, for example, with antioxidants, perfume oils, agents to prevent foaming, colorants, pigments that have a colouring action, thickeners, surface-active substances, emulsifiers, plasticising substances, moistening and/or moisture-retaining substances, fats, oils, waxes or other conventional constituents of a cosmetic formulation, such as alcohols, polyols, polymers, foam stabilisers, electrolytes, organic solvents or silicone derivatives. According to the invention all conceivable antioxidants, perfume oils, agents to prevent foaming, colorants, pigments that have a colouring action, thickeners, surface-active substances, emulsifiers, plasticising substances, moistening and/or moisture-retaining substances, fats, oils, waxes, alcohols, polyols, polymers, foam stabilisers, electrolytes, organic solvents or silicone derivatives that are suitable or customary for cosmetic and/or dermatological applications can be used here.

A high content of treatment substances is usually advantageous in formulations containing histamine release inhibitors according to the invention for the topical prophylactic or cosmetic treatment of the skin. According to a preferred embodiment, the compositions contain one or more animal and/or vegetable treatment fats and oils, such as olive oil, sunflower oil, purified soya oil, palm oil, sesame oil, rapeseed oil, almond oil, borage oil, evening primrose oil, coconut oil, shea butter, jojoba oil, sperm oil, beef tallow, neatsfoot oil and lard, and also optionally further treatment constituents, such as, for example, fatty alcohols having 8-30 C atoms. The fatty alcohols used here can be saturated or unsaturated and straight-chain or branched. For example, decanol, decenol, octanol, octenol, dodecanol, dodecenol, octadienol, decadienol, dodecadienol, oleyl alcohol, ricinol (sic) alcohol, erucic alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol, as well the guerbet alcohols thereof, can be used, in which context it would be possible to extend this list arbitrarily by further structurally chemically related alcohols. The fatty alcohols preferably originate from natural fatty acids, and are usually prepared from the corresponding esters of the fatty acids by reduction. Furthermore, fatty alcohol fractions that are formed from naturally occurring fats and fat oils by reduction can be used, such as, for example, beef tallow, peanut oil, colza oil, cottonseed oil, soya oil, sunflower oil, palm kernel oil, linseed oil, maize oil, castor oil, rapeseed oil, sesame oil, cocoa butter and cocoa fat.

In addition, the treatment substances that can preferably be combined with the histamine release inhibitors according to the invention also include
- ceramides, ceramides being understood to be N-acylsphingosines (fatty acid amides of sphingosine) or synthetic analogues of such lipids (so-called pseudo-ceramides), which clearly improve the water retention capacity of the stratum corneum.
- phospholipids, for example soya lecithin, egg lecithin and cephalins
- Vaseline, paraffin and silicone oils; the latter include, inter alia, dialkyl- and alkylaryl-siloxanes, such as dimethylpolysiloxane and methylphenylpolysiloxane, as well as the alkoxylated and quaternised derivatives thereof.

Animal and/or vegetable hydrolysed proteins can advantageously also be added to the formulations containing the histamine release inhibitors according to the invention. In this regard, in particular elastin, collagen, keratin, lactoprotein, soya protein, oat protein, pea protein, almond protein and wheat protein fractions or corresponding hydrolysed proteins, but also the condensation products thereof with fatty acids, and also quaternised hydrolysed proteins are advantageous, the use of vegetable hydrolysed proteins being preferred.

Insofar as a cosmetic or dermatological formulation containing the histamine release inhibitors according to the invention is a solution or lotion, the solvents used can be:
- water or aqueous solutions;
- fatty oils, fats, waxes and other natural and synthetic fatty bodies, preferably esters of fatty acids with alcohols having a low C number, for example with isopropanol, propylene glycol or glycerol, or esters of fatty alcohols with alkanoic acids having a low C number or with fatty acids;
- alcohols, diols or polyols having a low C number, as well as the ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the abovementioned solvents are used. In the case of alcoholic solvents, water can be a further constituent.

Cosmetic formulations that contain histamine release inhibitors according to the invention can also contain antioxidants, it being possible to use all antioxidants suitable or customary for cosmetic and/or dermatological applications. Advantageously, the antioxidants are selected from the group consisting of amino acids (for example glycine, histidine, tyrosine, tryptophan) and the derivatives thereof, imidazoles (for example urocanic acid) and the derivatives thereof, peptides such as D, L-carnosine, D-carnosine, L-carnosine and the derivatives thereof (for example anserine), carotinoids, carotenes (for example α-carotene, β-carotene, lycopene) and the derivatives thereof, lipoic acid and the derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) as well as the salts thereof, dilauryl thiodipropionate, distearyl thiodipropionate, thiodipropionic acid and the derivatives thereof (esters, ethers, peptides, lipids, nucleotides, nucleosides and salts) and also sulphoximine compounds (for example buthionine sulphoximines, homocysteine sulphoximine, buthionine sulphones, penta-, hexa-, hepta-thionine suphoximine) in very low tolerated doses, and also (metal) chelating agents, for example α-hydroxy fatty acids, palmitic acid, phytic acid, lactoferrin, α-hydroxy acids (for example citric acid, lactic acid, malic acid), humic acid, bile acid, bile extracts, bilirubin, biliverdin, EDTA, EGTA and the derivatives thereof, unsaturated fatty acids and the derivatives thereof (for example γ-linolenic acid, linoleic acid, oleic acid), folic acid and the derivatives thereof, ubiquinone and ubiquinol and the derivatives thereof, Vitamin C and derivatives (for example ascorbyl palmitate, Mg ascorbyl phosphate, ascorbyl acetate), tocopherols and the derivatives thereof (for example Vitamin E acetate), Vitamin A and the derivatives thereof (Vitamin A palmitate) and also coniferyl benzoate of benzoin resin, rutinic acid and the derivatives thereof, ferrulic acid and the derivatives thereof, butylhydroxytoluene, butylhydroxyanisole, nordihydroguaiacic acid, nordihydroguaiaretic acid, trihydroxybutyrophenone, uric acid and the derivatives thereof, mannose and the derivatives thereof, zinc and the derivatives thereof (for example ZnO, ZnSO4 (sic)), selenium and the derivatives thereof (for example selenium methionine), stilbenes and the derivatives thereof (for example stilbene oxide, trans-stilbene oxide) and the derivatives (salts, esters, ethers, sugars, nucleotides, nucleosides, peptides and lipids) of the said active compounds that are suitable according to the invention.

Cosmetic formulations that contain histamine release inhibitors according to the invention can also contain vitamins and vitamin precursors, it being possible to use all vitamins and vitamin precursors suitable or customary for cosmetic and/or dermatological applications. Mention may be made here in particular of vitamins and vitamin precursors such as tocopherols, Vitamin A, nicotinic acid and nicotinomide, further vitamins of the B complex, in particular biotin, and Vitamin C. Furthermore, within this group pantothenyl alcohol and the derivatives thereof, in particular esters and ethers of pantothenyl alcohol, and also derivatives of pantothenyl alcohols obtained cationically, such as, for example, pantothenyl alcohol triacetate, pantothenyl alcohol, monoethyl ether and the monoacetate thereof and also cationic pantothenyl alcohol derivatives are preferably used.

Cosmetic formulations that contain histamine release inhibitors according to the invention can also contain active compounds having a skin lightening action. In this context all skin lightening active compounds that are suitable or customary for cosmetic and/or dermatological applications can be used according to the invention. Advantageous skin lightening active compounds are, to this extent, kojic acid, hydroquinone, arbutin, ascorbic acid, magnesium ascorbylphosphate, liquorice root extracts and the constituents thereof glabridin or licochalkon A, or extracts from Rumex and Ramulus species, extracts from pine species (Pinus) or extracts from Vitis species which contain, inter alia, skin-lightening stilbene derivatives.

Cosmetic formulations that contain histamine release inhibitors according to the invention can also contain active compounds having a skin-tanning action. To this extent all skin-tanning active compounds that are suitable or customary for cosmetic and/or dermatological applications can be used. Dihydroxyacetone (DHA; 1,3-dihydroxy-2-propanone) may be mentioned here by way of example. DHA can be either in monomer or in dimer form, the proportion of dimers being predominant in the crystalline form.

Cosmetic formulations that contain histamine release inhibitors according to the invention can also contain mono-, di- and oligo-saccharides, such as, for example, glucose, galactose, fructose, mannose, fructose (sic) and lactose.

Cosmetic formulations that contain histamine release inhibitors according to the invention can also contain plant extracts, which are usually prepared by extraction of the complete plant, but in individual cases are also prepared exclusively from blossom and/or leaves, wood, bark or roots of the plant. With regard to the plant extracts that can be used according to the invention, reference is made in particular to the extracts that are listed in the table starting on page 44 of the third edition of the Leiffaden zur Inhaltsstoffdeklaration kosmetischer Mittel (Guide to the Declaration of Constituents of Cosmetic Agents), published by the Industrieverband Körperpflegemittel und Waschmittel e.V. (IKW), Frankfurt. The extracts from aloe, Hamamelis, algae, oak bark, willow-herb, stinging nettles, dead nettles, hops, camomile, milfoil, arnica, calendula, burdock root, horse-tail, hawthorn, linden blossom, almonds, pine needles, horse chestnut, sandalwood, juniper, coconut, mango, apricot, orange, lemon, lime, grapefruit, apple, green tea, grapefruit seed, wheat, oats, barley, sage, thyme, basil, rosemary, birch, mallow, bitter-crass, willow bark, restharrow, coltsfoot, althaea, ginseng and ginger root are particularly advantageous. Amongst these, the extracts from aloe vera, camomile, algae, rosemary, calendula, ginseng, cucumber, sage, stinging nettles, linden blossom, arnica and Hamamelis are particularly preferred. Mixtures of two or more plant extracts can also be employed. Extraction agents that can be used for the preparation of the said plant extracts can be, inter alia, water, alcohols and mixtures thereof. Amongst the alcohols, lower alcohols, such as ethanol and isopropanol, but also polyhydric alcohols, such as ethylene glycol, propylene glycol and butylene glycol are preferred in this context, and specifically both as sole extracting agent and also in mixtures with water. The plant extracts can be used according to the invention in the pure form or also in dilute form.

Cosmetic formulations that contain histamine release inhibitors according to the invention can also contain anionic, cationic, non-ionic and/or amphoteric surfactants, especially if crystalline or microcrystalline solids, for example inorganic micropigments, are to be incorporated into the formulations according to the invention. Surfactants are amphiphilic substances that are able to dissolve organic, non-polar substances in water. In this context the hydrophilic parts of a surfactant molecule are usually polar functional groups, for example, $-COO^-$, $-OoSO_3^{2-}$, $-SO_3^-$, whilst the hydrophobic parts are, as a rule, non-polar hydrocarbon radicals. Surfactants are generally classified according to the nature and charge of the hydrophilic part of the molecule. Four groups can be differentiated here:

anionic surfactants,
cationic surfactants,
amphoteric surfactants and
non-ionic surfactants.

Anionic surfactants usually contain carboxylate, sulphate or sulphonate groups as functional groups. In aqueous solution they form negatively charged organic ions in the acid or neutral medium. Cationic surfactants are characterised virtually exclusively by the presence of a quaternary ammonium group. In aqueous solution they form positively charged organic ions in the acid or neutral medium. Amphoteric surfactants contain both anionic and cationic groups and accordingly behave like anionic or cationic surfactants in aqueous solution, depending on the pH value. They have a positive charge in a strongly acid medium and a negative charge in an alkaline medium. In the neutral pH range, on the other hand, they are zwitter ionic. Polyether chains are typical of non-ionic surfactants. Non-ionic surfactants do not form ions in an aqueous medium.

A. Anionic Surfactants

Anionic surfactants that can advantageously be used are acylamino acids (and the salts thereof), such as
  acylglutamates, for example sodium acylgultamate, di-TEA-palmitoyl aspartate and sodium capryl/caprin glutamate,
  acylpeptides, for example palmitoyl-hydrolysed lactoprotein, sodium cocoyl-hydrolysed soya protein and sodium/potassium cocoyl-hydrolysed collagen,
  sarcosinates, for example myristoyl sarcosine, TEA lauroyl sarcosinate, sodium lauroyl sarcosinate and sodium cocoyl sarcosinate,
  taurates, for example sodium lauroyl taurate and sodium methylcocoyl taurate,
  acyl lactylates, lauroyl lactylate, caproyl lactylate
  alaninates
carboxylic acids and derivatives, such as,
  for example, lauric acid, aluminium stearate, magnesium alkanolate and zinc undecylenate,
  ester-carboxylic acids, for example calcium stearoyl lactylate, laureth-6 citrate and sodium PEG-4 lauramidocarboxylate,
  ether-carboxylic acids, for example sodium laureth-13 carboxylate and sodium PEG-6 cocamide carboxylate,
phosphoric acid esters and salts, such as, for example, DEA-oleth-10 phosphate and dilaureth-4 phosphate,
sulphonic acids and salts, such as
  acyl isothionates, for example sodium/ammonium cocoyl-isethionate,
  alkylarylsulphonates, alkylsulphonates, for example sodium coconut monoglyceride sulphate, sodium $C_{12-14}$ olefin-sulphonate, sodium lauryl sulpho-acetate and magnesium PEG-3 cocamidosulphate, sulphosuccinates, for example dioctylsodium sulphosuccinate, disodium laureth-sulphosuccinate, disodium laurylsulphosuccinate and disodium undecylenamido MEA-sulphosuccinate and sulphuric acid esters, such as
  alkyl ether sulphate, for example sodium, ammonium, magnesium, MIPA, TIPA laureth sulphate, sodium myreth sulphate and sodium C12-13 pareth sulphate,
  alkyl sulphates, for example sodium, ammonium and TEA lauryl sulphate.

B. Cationic Surfactants

Cationic surfactants that can advantageously be used are
  alkylamines,
  alkylimidazoles,
  ethoxylated amines and
  quaternary surfactants.

$$RNH_2CH_2CH_2COO^- \text{ (at pH=7)}$$

$$RNHCH_2CH_2COO^- \ B^+ \text{ (at pH=12) } B^+\text{=arbitrary cation, for example } Na^+$$

esterquats

Quaternary surfactants contain at least one N atom that is covalently bonded to 4 alkyl or aryl groups. This leads to a positive charge, irrespective of the pH value. Alkylbetaine, alkylamidopropylbetaine and alkylamidopropylhydroxysulfaine are advantageous. The cationic surfactants used can furthermore preferably be chosen from the group comprising the quaternary ammonium compounds, in particular benzyltrialkyl-ammonium chloride or bromide, such as, for example, benzyldimethylstearyl-ammonium chloride, and also alkyltrialkyl-ammonium salts, for example cetyltrimethylammonium chloride or bromide, alkyldimethylhydroxyethylammonium chlorides or bromides, dialkyldimethylammonium chlorides or bromides, alkylamidoethyl-trimethyl-ammonium ether sulphates, alkylpyridinium salts, for example lauryl- or cetylpyrimidinium chloride, imidazoline derivatives and compounds of a cationic nature, such as amine oxides, for example alkyldimethylamine oxides or alkylaminoethyldimethylamine oxides. Cetyltrimethylammonium salts can be used particularly advantageously.

C. Amphoteric Surfactants

Amphoteric surfactants that can advantageously be used are
  acyl-/dialkylethylenediamine, for example sodium acyl-lampho-acetate, disodium acylamphodipropionate, disodium alkylampho-diacetate, sodium acylamphohydroxypropylsulphonate, disodium acylamphodiacetate and sodium acylamphopropionate,
  N-alkylamino acids, for example aminopropylalkylglutamide, alkyl-aminopropionic acid, sodium alkylimidodipropionate and lauro-amphocarboxyglycinate.

D. Non-Ionic Surfactants

Non-ionic surfactants that can advantageously be used are
  alcohols,
  alkanolamides, such as cocamides MEA/DEA/MIPA,
  amine oxides, such as cocoamidopropylamine oxide,
  esters, that are formed by esterification of carboxylic acids with ethylene oxide, glycerol, sorbitan or other alcohols,
  ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkylpolyglycosides, such as lauryl glucoside, decyl glycoside and coco glycoside.
  sucrose esters and ethers
  polyglycerol esters, diglycerol esters, monoglycerol esters
  methylglucose esters, ester of hydroxy acids The use of a combination of anionic and/or amphoteric surfactants with one or more non-ionic surfactants is also advantageous. The surface-active substance can be present in a concentration of between 1 and 98% (m/m) in the formulations containing histamine release inhibitors according to the invention, based on the total weight of the formulations.

Cosmetic or dermatological formulations that contain histamine release inhibitors according to the invention can also be in the form of emulsions.

The oil phase can advantageously be chosen from the following group of substances:
  mineral oils, mineral waxes
  fatty oils, fats, waxes and other natural and synthetic fatty bodies, preferably esters of fatty acids with alcohols having a low C number, for example with isopropanol, propylene glycol or glycerol, or esters of fatty alcohols with alkanoic acids having a low C number or with fatty acids;
  alkyl benzoates;
  silicone oils, such as dimethylpolysiloxanes, diethylpolysiloxanes, diphenylpolysiloxanes and mixed forms therefrom.

Advantageously, esters of saturated and/or unsaturated, branched and/or straight-chain alkanecarboxylic acids having a chain length of 3 to 30 C atoms and saturated and/or unsaturated, branched and/or straight-chain alcohols having a chain length of 3 to 30 C atoms, from the group of esters of aromatic carboxylic acids and saturated and/or unsaturated, branched and/or straight-chain alcohols having a chain length of 3 to 30 C atoms can be used. Preferred ester oils are isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of such esters, for example, jojoba oil.

Furthermore, the oil phase can advantageously be chosen from the group comprising the branched and straight-chain hydrocarbons and waxes, the silicone oils, the dialkyl ethers, the group comprising the saturated or unsaturated, branched or straight-chain alcohols, and also the fatty acid triglycerides, specifically, the triglycerol esters of saturated and/or unsaturated, branched and/or straight-chain alkanecarboxylic acids having a chain length of 8 to 24, in particular 12 to 18 C atoms. The fatty acid triglycerides can, for example, advantageously be chosen from the group comprising the synthetic, semi-synthetic and natural oils, for example, olive oil, sunflower oil, soya oil, peanut oil, rapeseed oil, almond oil, palm oil, coconut oil, palm kernel oil and more of the like. Arbitrary admixtures of such oil and wax components can also advantageously be used. In some cases it is also advantageous to use waxes, for example cetyl palmitate, as the sole lipid component of the oil phase; advantageously, the oil phase is chosen from the group that consists of 2-ethylhexyl isostearate, octyldodecanol, isotridecyl isononanoate, isoeicosane, 2-ethylhexyl cocoate, $C_{12-15}$-alkyl benzoate, capryl-capric acid triglyceride and dicaprylyl ether. Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous. The hydrocarbons paraffin oil, squalane and squalene can oh (sic) advantageously be used. Advantageously, the oil phase can furthermore contain cyclic or linear silicone oils or consist entirely of such oils, it being, however, preferred to use an additional content of other oil phase components in addition to the silicone oil or the silicone oils. Cyclomethicone (for example, decamethylcyclopentasiloxane) can advantageously be used as silicone oil. However, other silicone oils can also advantageously be used, for example undecamethylcyclotrisiloxane, polydimethylsiloxane and poly(methylphenylsiloxane). Furthermore, mixtures of cyclomethicone and isotridecyl isononanoate and of cyclomethicone and 2-ethylhexyl isostearate are particularly advantageous.

The aqueous phase of formulations that contain histamine release inhibitors according to the invention and are in the form of an emulsion can comprise: alcohols, diols or polyols having a low C number and also the ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols having a low C number, for example, ethanol, isopropanol, 1,2-propanediol, glycerol and also, in particular, one or more thickeners, which thickener or thickeners can advantageously be chosen from the group comprising silicon dioxide, aluminium silicates, polysaccharides and the derivatives thereof, for example hyaluronic acid, xanthan gum, hydroxypropyl-methylcellulose, and particularly advantageously from the group comprising the polyacrylates, preferably a polyacrylate from the group comprising the so-called carbopols, for example carbopols of types 980, 981, 1382, 2984, 5984, in each case on their own or in combination.

Formulations that contain histamine release inhibitors according to the invention and are in the form of an emulsion advantageously contain one or more emulsifiers. O/W emulsifiers can, for example, advantageously be chosen from the group comprising the polyethoxylated or polypropoxylated or polyethoxylated and polypropoxylated products, for example:
the fatty alcohol ethoxylates
the ethoxylated wool wax alcohols,
the polyethylene glycol ethers of the general formula
R—O—(—CH$_2$—CH$_2$—O—)$_n$—R',
the fatty acid ethoxylates of the general formula
R—COO—(—CH$_2$—CH$_2$—O—)$_n$—H,
the etherified fatty acid ethoxylates of the general formula R—COO—(—CH$_2$—CH$_2$—O—)$_n$—R', the esterified fatty acid ethoxylates of the general formula R—COO—(—CH$_2$—CH$_2$—O—)$_n$—C(O)—R', the polyethylene glycol glycerol fatty acid esters
the ethoxylated sorbitan esters
the cholesterol ethoxylates
the ethoxylated triglycerides
the alkyl ether carboxylic acids of the general formula R—COO—(—CH$_2$—CH$_2$—O—)$_n$—OOH, and n represent (sic) a number from 5 to 30, the polyoxyethylene sorbitol fatty acid esters,
the alkyl ether sulphates of the general formula R—O—(—CH$_2$—CH$_2$—O—)$_n$—SO$_3$—H the fatty alcohol propoxylates of the general formula R—O—(—CH$_2$—CH(CH$_3$)—O—)$_n$—H the polypropylene glycol ethers of the general formula R—O—(—CH$_2$—CH(CH$_3$)—O—)$_n$—R' the propoxylated wool wax alcohols,
the esterified fatty acid propoxylates R—COO—(—CH$_2$—CH(CH$_3$)—O—)$_{n-R'}$
the esterified fatty acid propoxylates of the general formula R—COO—(—CH$_2$—CH(CH$_3$)—O—)$_n$—C(O)—R' the fatty acid propoxylates of the general formula

R—COO—(—CH$_2$—CH(CH$_3$)—O—)$_n$—H, the polypropylene glycol glycerol fatty acid esters
the propoxylated sorbitan esters
the cholesterol propoxylates
the propoxylated triglycerides
the alkyl ether carboxylic acids of the general formula R—O—(—CH$_2$—CH(CH$_3$)—O—)$_n$—CH$_2$—COOH, the alkyl ether sulphates and the acids on which these sulphates are based of the general formula R—O—(—CH$_2$—CH(CH$_3$)—O—)$_n$—SO$_3$—H,
the fatty alcohol ethoxylates/propoxylates of the general formula R—O—X$_n$—Y$_m$—H
the polypropylene glycol ethers of the general formula R—O—X$_n$—Y$_m$—R'
the esterified fatty acid propoxylates of the general formula R—COO—X$_n$—Y$_m$—R'
the fatty acid ethoxylates/propoxylates of the general formula R—COO—X$_n$—Y$_m$—H.

According to the invention, the polyethoxylated or polypropoxylated or polyethoxylated and polypropoxylated O/W emulsifiers used are particularly advantageously chosen from the group comprising substances having HLB values of 11-18, very particularly advantageously having HLB values of 14.5-15.5, insofar as the O/W emulsifiers contain saturated radicals R and R'. If the O/W emulsifiers contain unsaturated radicals R and/or R', or if there are isoalkyl derivatives, the preferred HLB value of such emulsifiers can also be lower or higher.

It is advantageous to choose the fatty alcohol ethoxylates from the group comprising the ethoxylated stearyl alcohols, cetyl alcohols, cetylstearyl alcohols (cetearyl alcohols). The following are particularly preferred:
polyethylene glycol(13) stearyl ether (Steareth-13),
polyethylene glycol(14) stearyl ether (Steareth-14),
tpolyethylene glycol(15) stearyl ether (Steareth-15),
polyethylene glycol(16) stearyl ether (Steareth-16),
polyethylene glycol(17) stearyl ether (Steareth-17),
polyethylene glycol(18) stearyl ether (Steareth-18),
polyethylene glycol(19) stearyl ether (Steareth-19),
polyethylene glycol(20) stearyl ether (Steareth-20),
polyethylene glycol(12) isostearyl ether (Isosteareth-12),
polyethylene glycol(13) isostearyl ether (Isosteareth-13),
polyethylene glycol(14) isostearyl ether (Isosteareth-14),
polyethylene glycol(15) isostearyl ether (Isosteareth-15),
polyethylene glycol(16) isostearyl ether (Isosteareth-16),
polyethylene glycol(17) isostearyl ether (Isosteareth-17),
polyethylene glycol(18) isostearyl ether (Isosteareth-18),
polyethylene glycol(19) isostearyl ether (Isosteareth-19),
polyethylene glycol(20) isostearyl ether (Isosteareth-20),
polyethylene glycol(13) cetyl ether (Ceteth-13),
polyethylene glycol(14) cetyl ether (Ceteth-14),
polyethylene glycol(15) cetyl ether (Ceteth-15),
polyethylene glycol(16) cetyl ether (Ceteth-16), polyethylene glycol(17) cetyl ether (Ceteth-17),
polyethylene glycol(18) cetyl ether (Ceteth-18),
polyethylene glycol(19) cetyl ether (Ceteth-19),
polyethylene glycol(20) cetyl ether (Ceteth-20),
polyethylene glycol(13) isocetyl ether (Isoceteth-13),
polyethylene glycol(14) isocetyl ether (Isoceteth-14),
polyethylene glycol(l15) isocetyl ether (Isoceteth-15),
polyethylene glycol(16) isocetyl ether (Isoceteth-16),
polyethylene glycol(17) isocetyl ether (Isoceteth-17),
polyethylene glycol(18) isocetyl ether (Isoceteth-18),
polyethylene glycol(19) isocetyl ether (Isoceteth-19),
polyethylene glycol(20) isocetyl ether (Isoceteth-20),
polyethylene glycol(12) oleyl ether (Oleth-12),
polyethylene glycol(13) oleyl ether (Oleth-13),
polyethylene glycol(14)oleyl ether (Oleth-14),
polyethylene glycol(15)oleyl ether (Oleth-15),
polyethylene glycol(12) lauryl ether (Laureth-12),
polyethylene glycol(12) isolauryl ether (Isolaureth12),
polyethylene glycol(13) cetyl stearyl ether (Ceteareth-13),
polyethylene glycol(14) cetyl stearyl ether (Ceteareth-14),
polyethylene glycol(15) cetyl stearyl ether (Ceteareth-15),
polyethylene glycol(16) cetyl stearyl ether (Ceteareth-16),
polyethylene glycol(17) cetyl stearyl ether (Ceteareth-17),
polyethylene glycol(18) cetyl stearyl ether (Ceteareth-18),
polyethylene glycol(19) cetyl stearyl ether (Ceteareth-19),
polyethylene glycol(20) cetyl stearyl ether (Ceteareth-20).

It is furthermore advantageous to choose the fatty acid ethoxylates from the following group:
polyethylene glycol(20) stearate,
polyethylene glycol(21) stearate,
polyethylene glycol(22) stearate,
polyethylene glycol(23) stearate,
polyethylene glycol(24) stearate,
polyethylene glycol(25) stearate,
polyethylene glycol(12) isostearate,
polyethylene glycol(13) isostearate,
polyethylene glycol(14) isostearate,
polyethylene glycol(15) isostearate,
polyethylene glycol(16) isostearate,
polyethylene glycol(17) isostearate,
polyethylene glycol(18) isostearate,
polyethylene glycol(19) isostearate,
polyethylene glycol(20) isostearate,
polyethylene glycol(21) isostearate,
polyethylene glycol(22) isostearate,
polyethylene glycol(23) isostearate,
polyethylene glycol(24) isostearate,
polyethylene glycol(25) isostearate,
polyethylene glycol(12) oleate,
polyethylene glycol(13) oleate,
polyethylene glycol(14) oleate,
polyethylene glycol(15) oleate,
polyethylene glycol(16) oleate,
polyethylene glycol(17) oleate,
polyethylene glycol(18) oleate,
polyethylene glycol(19) oleate,
polyethylene glycol(20) oleate.

Advantageously, sodium laureth-11-carboxylate can be used as ethoxylated alkyl ether carboxylic acid or the salt thereof. Sodium laureth 1-4 sulphate can advantageously be used as alkyl ether sulphate. Polyethylene glycol(30) cholesteryl ether can advantageously be used as ethoxylated cholesterol derivative. Polyethylene glycol(25) soyasterol has also proved useful.

The polyethylene glycol(60) evening primrose glycerides can advantageously be used as ethoxylated triglycerides.

It is furthermore advantageous to choose the polyethylene glycol glycerol fatty acid esters from the group comprising
polyethylene glycol(20) glyceryl laurate,
polyethylene glycol(21) glyceryl laurate,
polyethylene glycol(22) glyceryl laurate,
polyethylene glycol(23) glyceryl laurate,
polyethylene glycol(6) glyceryl caprate/caprinate,
polyethylene glycol(20) glyceryl oleate,
polyethylene glycol(20) glyceryl isostearate,
polyethylene glycol(18) glyceryl oleate/cocoate.

It is also advantageous to choose the sorbitan esters from the group comprising
polyethylene glycol(20) sorbitan monolaurate,
polyethylene glycol(20) sorbitan monostearate,
polyethylene glycol(20) sorbitan monoisostearate,
polyethylene glycol(20) sorbitan monopalmitate,
polyethylene glycol(20) sorbitan monooleate.

The following can be used as advantageous W/O emulsifiers: fatty alcohols having 8 to 30 carbon atoms, monoglycerol esters of saturated and/or unsaturated, branched and/or straight-chain alkanecarboxylic acids having a chain length of 8 to 24, in particular 12 to 18 C atoms, diglycerol esters of saturated and/or unsaturated, branched and/or straight-chain alkanecarboxylic acids having a chain length of 8 to 24, in particular 12 to 18 C atoms, monoglycerol ethers of saturated and/or unsaturated, branched and/or straight-chain alcohols having a chain length of 8 to 24, in particular 12 to 18 C atoms, diglycerol ethers of saturated and/or unsaturated, branched and/or straight-chain alcohols having a chain length of 8 to 24, in particular 12 to 18 C atoms, propylene glycol esters of saturated and/or unsaturated, branched and/or straight-chain alkanecarboxylic acids having a chain length of 8 to 24, in particular 12 to 18 C atoms and sorbitan esters of saturated and/or unsaturated, branched and/or straight-chain alkanecarboxylic acids having a chain length of 8 to 24, in particular 12 to 18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol(2) stearyl ether (Steareth-2), glyceryl monolaurate, glyceryl monocaprinate, glyceryl monocaprylate.

The substance of the Formula 1 according to the invention can also be used as a constituent of perfume compositions (fragrance compositions) and, because of its specific activity, as an inhibitor of substance P-induced release of histamine from mast cells can, for example, impart an anti-allergic or itch-alleviating action to a perfumed finished product. A particularly preferred fragrance composition comprises (a) a fragrance in an amount that has a sensory action, (b) an amount of one or more compounds of the Formula 1 that has, for example an anti-allergic or itch-alleviating action and (c) optionally one or more excipients and/or additives. Since the proportion of perfume in a cosmetic finished product is frequently in the region of approximately 1% (m/m), a perfume which contains a compound of the Formula 1 according to the invention will preferably consist of approximately 0.1-10% (m/m) of one or more compounds of the Formula 1. It has proved particularly advantageous that the substances of the Formula 1 have only a weak inherent odour or are even completely odourless; since this characteristic predestines them in particular for use as inhibitors of the substance P-induced release of histamine from mast cells in a fragrance composition.

Preferred embodiments and further aspects of the present invention can be seen from the appended patent claims.

TABLE 1a

| No. | Structural formula | % inhibition | | |
| --- | --- | --- | --- | --- |
| | | 0.5 ppm | 5 ppm | 50 ppm |
| 2 | | 7 | 80 | 108 |
| 3 | | 11 | 62 | 106 |
| 4 | | 3 | 49 | 59 |
| 5 | | 7 | 17 | 47 |
| 6 | | −9 | 1 | 41 |
| 7 | | 27 | 26 | 40 |
| 8 | | 13 | 26 | 40 |
| 9 | | 11 | 19 | 39 |

TABLE 1a-continued

| No. | Structural formula | % inhibition | | |
| --- | --- | --- | --- | --- |
| | | 0.5 ppm | 5 ppm | 50 ppm |
| 10 | 4-HO-C6H4-CH=CH-C(O)NH-C6H4-2-CO2H | −10 | 8 | 37 |
| 11 | 3,4-(MeO)2-C6H3-CH2CH2-C(O)NH-C6H3(2-CO2H)(5-OH) | −6 | 11 | 36 |
| 12 | C6H5-CH=CH-C(O)NH-C6H3(2-CO2H)(5-OH) | −5 | 0 | 34 |
| 13 | 3,4-(MeO)2-C6H3-CH=CH-C(O)NH-C6H3(2-CO2H)(5-OH) | 17 | 2 | 30 |
| 14 | 4-MeO-C6H4-CH=CH-C(O)NH-C6H4-2-CO2H | 21 | 30 | 24 |
| 15 | 3,4-(MeO)2-C6H3-CH=CH-C(O)NH-C6H4-2-CO2H | 23 | 22 | 21 |
| 16 | 3,4-(MeO)2-C6H3-CH2CH2-C(O)NH-C6H4-2-CO2Me | 26 | 25 | 7 |
| 17 | C6H5-CH=CH-C(O)NH-C6H4-2-CO2H | 4 | 7 | 6 |

TABLE 1a-continued

| No. | Structural formula | % inhibition | | |
|---|---|---|---|---|
| | | 0.5 ppm | 5 ppm | 50 ppm |
| 18 | MeO-, MeO- substituted cinnamoyl-NH-C6H4-CO2Me | 5 | −3 | 6 |
| 19 | MeO-, MeO- substituted phenylpropanoyl-NH-C6H4-CO2H | −15 | −22 | −4 |

TABLE 1b

| No. | Structural formula | % inhibition | | |
|---|---|---|---|---|
| | | 0.5 ppm | 5 ppm | 50 ppm |
| 20 | 3,4-dihydroxybenzoyl-NH-C6H4-CO2H | 14 | 76 | 110 |
| 21 | 4-hydroxybenzoyl-NH-C6H3(OH)-CO2H | −15 | 48 | 76 |
| 22 | 3,4,5-trihydroxybenzoyl-NH-C6H4-CO2H | 39 | 72 | 71 |
| 23 | 3-hydroxy-4-methoxybenzoyl-NH-C6H4-CO2H | 9 | 29 | 69 |
| 24 | 4-hydroxybenzoyl-NH-C6H4-CO2H | 7 | 19 | 55 |

TABLE 1b-continued

| No. | Structural formula | % inhibition | | |
| --- | --- | --- | --- | --- |
| | | 0.5 ppm | 5 ppm | 50 ppm |
| 25 | MeO, HO-benzamide-C6H4-CO2H (3-methoxy-4-hydroxybenzoyl anthranilic acid) | 8 | 42 | 51 |
| 26 | HO, OH-benzamide-C6H4-CO2H (2,4-dihydroxybenzoyl anthranilic acid) | −13 | 22 | 48 |
| 27 | benzamide-C6H4-CO2H | 27 | 28 | 39 |
| 28 | 3-HO-benzamide-C6H4-CO2H | 12 | 25 | 35 |
| 29 | 2-OH-benzamide-C6H4-CO2H | −1 | 15 | 23 |

TABLE 2

GS101100-A: Anthranilic acid amide fraction from cultivated oats extract
Anthranilic acid amide content (sum of avenanthramides 3, 4 and 5) = 500 ppm in glycerol
GS101100-B: Rconstituted product consisting of synthetic avenathramides 3, 4 and 5
Anthranilic acid amide content (sum of synthetic avenanthramides 3, 4 and 5) = 500 ppm in glycerol

| No. | Structural formula | % inhibition | | |
| --- | --- | --- | --- | --- |
| | | 0.5 ppm | 5 ppm | 50 ppm |
| GS101100-A | Cultivated oats extract fraction | 57.80 | 30.00 | 111.30 |
| GS101100-B | (3,4-dihydroxycinnamoyl + 3-methoxy-4-hydroxycinnamoyl anthranilic acid derivatives with 4-OH, 2-CO2H) | 1.20 | 30.50 | 116.50 |

TABLE 2-continued

GS101100-A: Anthranilic acid amide fraction from cultivated oats extract
Anthranilic acid amide content (sum of avenanthramides 3, 4 and 5) = 500 ppm in glycerol
GS101100-B: Rconstituted product consisting of synthetic avenathramides 3, 4 and 5
Anthranilic acid amide content (sum of synthetic avenanthramides 3, 4 and 5) = 500 ppm in glycerol

| No. | Structural formula | % inhibition | | |
|---|---|---|---|---|
| | | 0.5 ppm | 5 ppm | 50 ppm |
| | 3-(4-hydroxyphenyl)propanoyl-amino-hydroxybenzoic acid structure | | | |

TABLE 3

| No. | Structural formula | Chemical name |
|---|---|---|
| 5 | | 5-hydroxy-2-{[3-(4-hydroxyphenyl)propanoyl]amino)benzoic acid |
| 8 | | 2-{[3-(4-hydroxyphenyl)propanoyl]amino}benzoic acid |
| 11 | | 5-hydroxy-2-{[3-(3,4-dimethoxyphenyl)propanoyl]amino}benzoic acid |
| 20 | | 2-[(3,4-dihydroxybenzoyl)amino]benzoic acid |
| 22 | | 2-[(3,4,5-trihydroxybenzoyl)amino]benzoic acid |
| 23 | | 2-[(3-hydroxy-4-methoxybenzoyl)amino]-benzoic acid |

TABLE 3-continued

| No. | Structural formula | Chemical name |
|---|---|---|
| 24 | | 2-[(4-hydroxy-benzoyl)amino]benzoic acid |
| 25 | | 2-[(4-hydroxy-3-methoxybenzoyl)amino]-benzoic acid |
| 28 | | 2-[(3-hydroxy-benzoyl)amino]benzoic acid |
| 36 | | 2-{[3-(3,4-dihydroxy-phenyl)propano-yl]amino}benzoic acid |
| 37 | | 5-hydroxy-2-{[3-(3,4-dihydroxyphenyl)propa-noyl]amino}benzoic acid |
| 38 | | 4-hydroxy-2-{[3-(3,4-dihydroxyphenyl)propa-noyl]amino}benzoic acid |
| 39 | | 2-{[3-(4-hydroxy-3-methoxyphenyl)propa-noyl]amino}benzoic acid |
| 40 | | 5-hydroxy-2-{(3-(4-hydroxy-3-methoxy-phenyl)propano-yl]amino}benzoic acid |

TABLE 3-continued

| No. | Structural formula | Chemical name |
|---|---|---|
| 41 | | 4-hydroxy-2-{[3-(4-hydroxy-3-methoxyphenyl)propanoyl]amino}benzoic acid |
| 42 | | 4-hydroxy-2-{[3-(4-hydroxyphenyl)propanoyl]amino}benzoic acid |
| 43 | | 5-hydroxy-2-{[3-(3-hydroxy-4-methoxyphenyl)allanoyl]amino}benzoic acid |
| 44 | | 4-hydroxy-2-{[3-(3-hydroxy-4-methoxyphenyl)allanoyl]amino}benzoic acid |
| 45 | | 2-{[3-(3-hydroxy-4-methoxyphenyl)propanoyl]amino}benzoic acid |
| 46 | | 5-hydroxy-2-{[3-(3-hydroxy-4-methoxyphenyl)propanoyl]amino}benzoic acid |
| 47 | | 4-hydroxy-2-{[3-(3-hydroxy-4-methoxyphenyl)propanoyl]amino}benzoic acid |

TABLE 3-continued

| No. | Structural formula | Chemical name |
|---|---|---|
| 48 | | 2-{[3-(2,4-dihydroxy-phenyl)allano-yl]amino}benzoic acid |
| 49 | | 2-{[3-(2,4-dihydroxy-phenyl)propano-yl]amino}benzoic acid |
| 50 | | 5-hydroxy-2-{[3-(2,4-dihydroxyphenyl)allano-yl]amino}benzoic acid |
| 51 | | 5-hydroxy-2-{[3-(2,4-dihydroxyphenyl)propa-noyl]amino}benzoic acid |
| 52 | | 4-hydroxy-2-{[3-(2,4-dihydroxyphenyl)allano-yl]amino}benzoic acid |
| 53 | | 4-hydroxy-2-{[3-(2,4-dihydroxyphenyl)propa-noyl]amino}benzoic acid |
| 54 | | 2-{[3-(3-hydroxyphenyl)allano-yl]amino}benzoic acid |
| 55 | | 2-{[3-(3-hydroxyphenyl)propano-yl]amino}benzoic acid |

TABLE 3-continued

| No. | Structural formula | Chemical name |
|---|---|---|
| 56 | | 5-hydroxy-2-{[3-(3-hydroxyphenyl)allanoyl]amino}benzoic acid |
| 57 | | 5-hydroxy-2-{[3-(2,4-dihydroxyphenyl)propanoyl]amino benzoic acid |
| 58 | | 4-hydroxy-2-{[3-(3-hydroxyphenyl)allanoyl]amino}benzoic acid |
| 59 | | 4-hydroxy-2-{[3-(2,4-dihydroxyphenyl)propanoyl]amino}benzoic acid |
| 60 | | 2-{[3-(2-hydroxyphenyl)allanoyl]amino}benzoic acid |
| 61 | | 2-{[3-(2-hydroxyphenyl)propanoyl]amino}benzoic acid |
| 62 | | 5-hydroxy-2-{[3-(2-hydroxyphenyl)allanoyl]amino}benzoic acid |
| 63 | | 5-hydroxy-2-{[3-(2-hydroxyphenyl)propanoyl]amino}benzoic acid |

TABLE 3-continued

| No. | Structural formula | Chemical name |
|---|---|---|
| 64 | | 4-hydroxy-2-{[3-(2-hydroxyphenyl)allano-yl]amino}benzoic acid |
| 65 | | 4-hydroxy-2-{[3-(2-hydroxyphenyl)propano-yl]amino}benzoic acid |
| 66 | | 5-hydroxy-2-[(3,4,5-trihydroxybenzo-yl)amino]benzoic acid |
| 67 | | 4-hydroxy-2-[(3,4,5-trihydroxybenzo-yl)amino]benzoic acid |
| 68 | | 5-hydroxy-2-[(3,4-dihydroxybenzo-yl)amino]benzoic acid |
| 69 | | 4-hydroxy-2-[(3,4-dihydroxybenzo-yl)amino]benzoic acid |
| 70 | | 5-hydroxy-2-[(2,4-dihydroxybenzo-yl)amino]benzoic acid |

TABLE 3-continued

| No. | Structural formula | Chemical name |
|---|---|---|
| 71 | | 5-hydroxy-2-[(3-hydroxy-4-methoxy-benzoyl)amino]benzoic acid |
| 72 | | 4-hydroxy-2-[(3-hydroxy-4-methoxy-benzoyl)amino]benzoic acid |
| 73 | | 5-hydroxy-2-[(4-hydroxy-3-methoxy-benzoyl)amino]benzoic acid |
| 74 | | 4-hydroxy-2-[(4-hydroxy-3-methoxy-benzoyl)amino]benzoic acid |
| 75 | | 4-hydroxy-2-[(4-hydroxybenzoyl)amino]-benzoic acid |
| 76 | | 5-hydroxy-2-[(3-hydroxybenzoyl)amino]-benzoic acid |
| 77 | | 4-hydroxy-2-[(3-hydroxybenzoyl)amino]-benzoic acid |

TABLE 3-continued

| No. | Structural formula | Chemical name |
|---|---|---|
| 78 | | 5-hydroxy-2-[(2-hydroxybenzoyl)amino]-benzoic acid |
| 79 | | 5-hydroxy-2-[(benzoyl)amino]benzoic acid |
| 80 | | 4-hydroxy-2-[(benzoyl)amino]benzoic acid |

TABLE 4

| No. | Structural formula | CAS no. |
|---|---|---|
| 2 | | 116764-16-0 |
| 3 | | 116764-15-9 |
| 4 | | 108605-69-2 |
| 6 | | 116764-17-1 |

TABLE 4-continued

| No. | Structural formula | CAS no. |
|---|---|---|
| 7 | | 108605-70-5 |
| 9 | | 93755-77-2 |
| 10 | | 115610-36-1 |
| 12 | | 207742-91-4 |
| 13 | | 188545-62-2 |
| 21 | | 110846-17-8 |
| 26 | | 115610-37-2 |
| 27 | | 579-93-1 |

TABLE 4-continued

| No. | Structural formula | CAS no. |
| --- | --- | --- |
| 29 | | 13316-98-8 |
| 30 | | 448029-17-0 |
| 31 | | 116764-18-2 |
| 32 | | 116764-19-3 |
| 33 | | 80530-43-4 |
| 34 | | 115610-38-3 |
| 35 | | 115610-40-7 |

The invention claimed is:
1. Compound of the Formula 1,

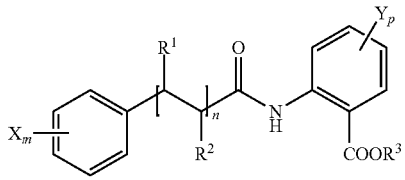

where:
  m=0, 1, 2 or 3,
  p=0 or 1,
  n=1,
  with the proviso that the sum of p +m >0,
  where $R^1$ and $R^2$ denote H;
  where, when m=1, 2 or 3, each X, independently of the others, denotes OH, Oalkyl or Oacyl,
  where, when p=1, Y denotes OH or Oalkyl,
  with the proviso that X has been selected at least once from the group that consists of OH and Oacyl or Y is OH;
  $R^3$=H or alkyl.

2. Compound of the Formula 1a,

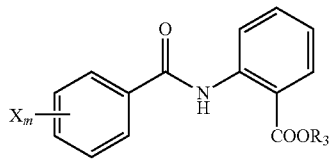

where:
  m=2,
  where, each X is independently Oalkyl or Oacyl,
  with the proviso that X has been selected once from Oacyl and once from Oalkyl;
  $R^3$=alkyl.

3. A compound according to claim 1, selected from the group consisting of:

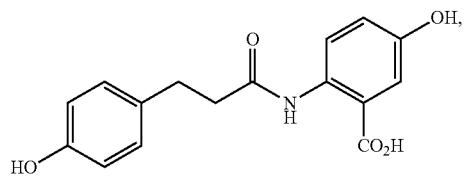

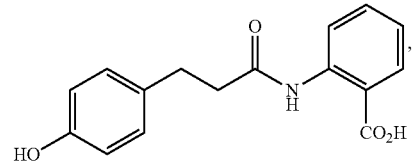

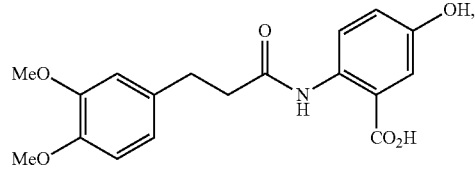

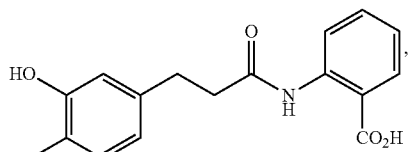

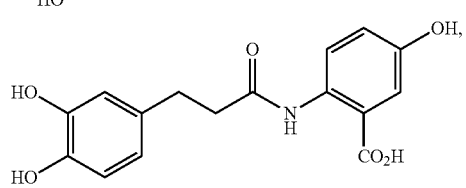

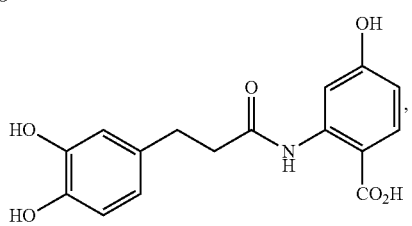

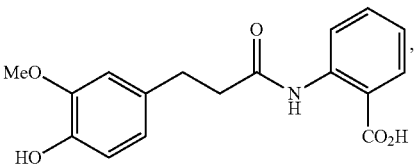

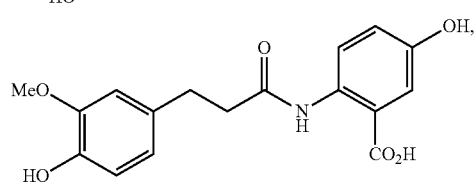

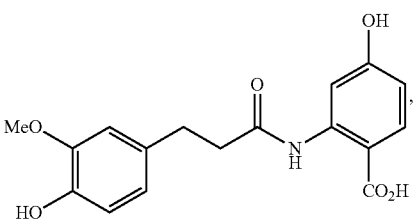

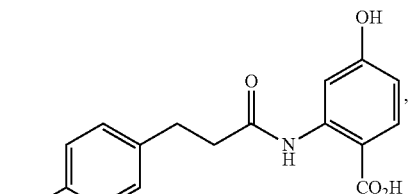

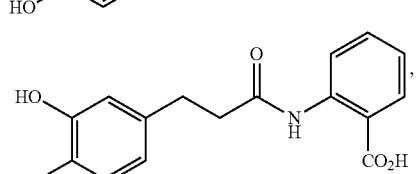

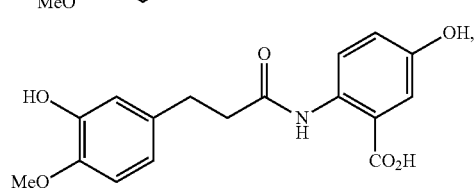

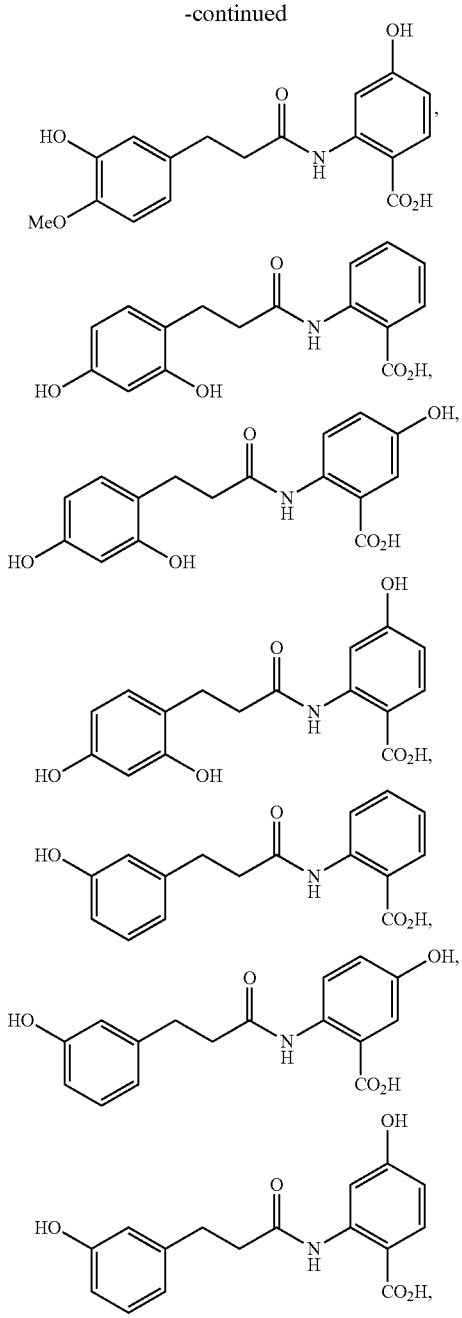

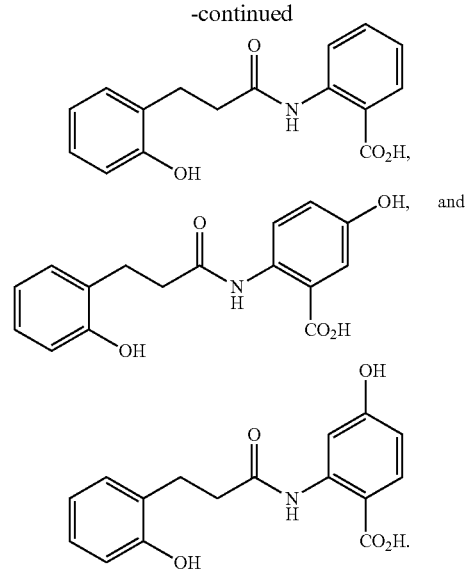

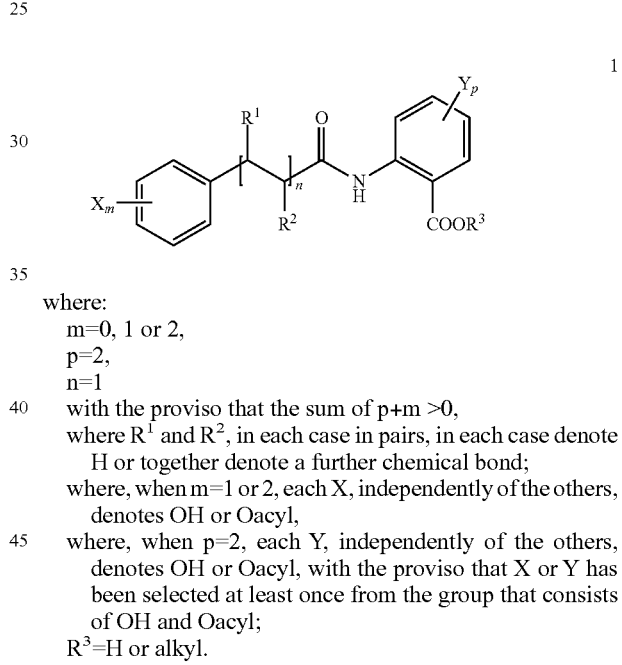

4. Compound of the Formula 1, $$\text{X}_m\text{—Ar—CR}^1\text{R}^2\text{—(CH)}_n\text{—C(O)—NH—Ar'—Y}_p\text{—COOR}^3$$

1 where:
m=0, 1 or 2,
p=2,
n=1
with the proviso that the sum of p+m >0,
where $R^1$ and $R^2$, in each case in pairs, in each case denote H or together denote a further chemical bond;
where, when m=1 or 2, each X, independently of the others, denotes OH or Oacyl,
where, when p=2, each Y, independently of the others, denotes OH or Oacyl, with the proviso that X or Y has been selected at least once from the group that consists of OH and Oacyl;
$R^3$=H or alkyl.

* * * * *